United States Patent [19]

Mallams et al.

[11] Patent Number: 4,851,518
[45] Date of Patent: Jul. 25, 1989

[54] DI AND TRI-O-ACETYL-"O-ISO-VALERYL-23-O-DEMYCINOSYL TYLOSINS, HYDRAZONE DERIVATIVES THEREOF AND PROCESSES FOR THEIR PREPARATION

[75] Inventors: Alan K. Mallams, West Orange; Randall R. Rossman, Nutley, both of N.J.

[73] Assignee: Schering Corporation, Kenilworth, N.J.

[21] Appl. No.: 812,148

[22] Filed: Dec. 23, 1985

[51] Int. Cl.$^4$ ............................................. C07H 17/08
[52] U.S. Cl. ........................................ 536/71; 536/124
[58] Field of Search ................. 514/30; 536/7.1, 124

[56] References Cited

U.S. PATENT DOCUMENTS

| | | | |
|---|---|---|---|
| 3,970,642 | 7/1976 | Freiberg | 536/7.1 |
| 4,001,399 | 1/1977 | Osono et al. | 536/7.1 |
| 4,017,607 | 4/1977 | Inouye et al. | 536/7.1 |
| 4,145,540 | 3/1979 | Ochiai et al. | 544/21 |
| 4,205,163 | 5/1980 | Mori et al. | 536/17 R |
| 4,321,361 | 3/1982 | Baltz et al. | 536/17 R |
| 4,396,613 | 8/1983 | Kirst | 424/180 |
| 4,436,729 | 3/1984 | Ganguly et al. | 424/180 |
| 4,436,733 | 3/1984 | Kirst | 424/180 |

FOREIGN PATENT DOCUMENTS 849847 2/1981 Belgium.
96990 12/1983 European Pat. Off..
60-16960 4/1985 Japan.
2077731 12/1981 United Kingdom.

OTHER PUBLICATIONS

H. Matsubara et al. Chem. Pharm. Bull., 1982, vol. 30, pp.97–110.
S. Omura et al. The Journal of Antibiotics, 1984, vol. XXXVII, pp. 1007–1015.
N. N. Girotra et al., Tetrahedron, 1976, vol. 32, pp. 991–993.
T. Suzuki et al., Chemistry Letters (Japan), 1973, pp. 793–748.
S. Omura et al. The Journal of Antibiotics, 1974, vol. XXVII, pp. 370–372.
A. Hassner et al. Tetrahedron, 1978, vol. 34, pp. 2069–2076.

Primary Examiner—Johnnie R. Brown
Assistant Examiner—Elli Peselev
Attorney, Agent, or Firm—Thomas D. Hoffman; Gerald S. Rosen

[57] ABSTRACT

There are disclosed novel di- and tri-O-acetyl-23-O-demycinosyl-4"-O-iso-valeryltylosins and the pharmaceutically acceptable salts thereof, which have improved activity as antibacterials and provide higher blood levels than other tylosin derived compounds. These compounds have the following structural formula

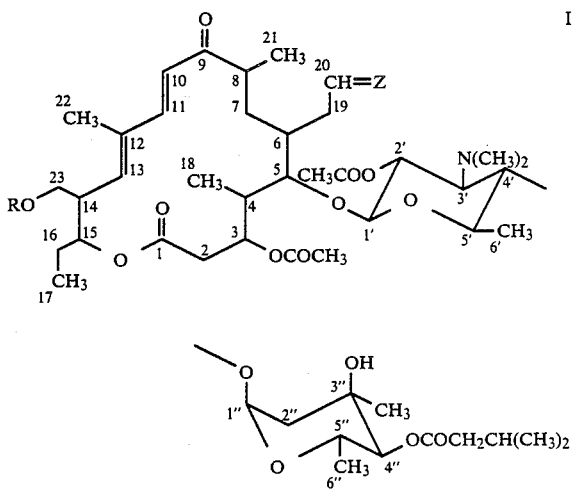

wherein R is acetyl or hydrogen and z is for example O or

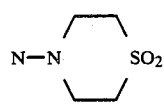

Processes for selectively deacylating the 2' and 4"-positions of 3,2',4",4"'-tetra-O-acyltylosin or 2',4",4"'-tri-O-acyltylosin and for the selective acylation of 2',4"-di-O-acyltylosin and 2',4",4"'-tri-O-acyltylosin are also disclosed.

10 Claims, No Drawings

DI AND TRI-O-ACETYL-"O-ISO-VALERYL-23-O-DEMYCINOSYL TYLOSINS, HYDRAZONE DERIVATIVES THEREOF AND PROCESSES FOR THEIR PREPARATION

BACKGROUND OF THE INVENTION

This invention relates to di and tri-O-acetyl-4"-O-iso-valeryl-23-O-demycinosyltylosins, hydrazone derivatives thereof and a process for their preparation. This invention also relates to processes for the preparation of di-, tri- and tetra-O-acyl-23-O-demycinosyltylosin derivatives. The present invention further relates to selective acylation processes for preparing 2',4",4'''-tri-O-acyltylosin and 3,2',4",4'''-tetra-O-acyltylosin and selective deacylation process for preparation of 3,4"-di-O-acyltylosin.

Tylosin and numerous derivatives thereof are known in the antibiotic art. However, tylosin and 23-O-demycinosyltylosin are readily transformed in acidic and basic solution into aldol condensation and Michael addition products. See for example H. Matsubara et al., *Chem. Pharm. Bull.* (Japan), Vol. 30, pp 97–110 (1982); S. Omura et al., *The Journal of Antibiotics*, Vol. XXXVII, pp 1007–1015 (1984); N.N. Girotra et al., *Tetrahedron*, Vol. 32, pp 991–993 (1976); T. Suzuki et al., *Chemistry Letters* (Japan), pp 793–798 (1973); and S. Omura et al. *The Journal of Antibiotics*, Vol. XXVII, pp 370–372 (1974). Accordingly, microbiological acylation and the use of labile acyl groups which can be easily and selectively removed have been utilized by prior art workers to avoid formation of side product.

U.S. Pat. No. 4,436,733 discloses a large genus of tylosin analogs. Specifically, it discloses 4"-and 3-mono- and 3,4"-di-O-acyl derivatives of 23-O-demycinosyltylosin and 23-demycinosyloxytylosin. The compounds of this invention are not specifically disclosed therein. The acylation procedure described in U.S. Pat. No. 4,436,733 requires use of highly labile acyl groups such as phenoxyacetyl and mono- and tri-haloacetyl.

A. Hassner et al. in *Tetrahedron*, Vol. 34, pp 2069–2076 (1978) disclose use of catalytic amounts (0.02 to 0.1 equivalents) amount of 4-aminopyridines such as 4-(dimethylamino)pyridine (DMAP) as acylation catalysts for unreactive alcohols at room temperature. U.S. Pat. No. 4,454,314 at col. 25, lines 53–65 discloses use of catalytic amounts of DMAP for selective acylation of the C-3 secondary hydroxyl group of tylosin derivative.

UK Patent Application 2,077,731 discloses 23-O-demycinosyltylosin and its 20-dihydro derivatives which are allegedly useful against Gram-positive bacteria and *Mycoplasma* species. In the compounds disclosed, when the 3-position of the molecule is occupied by an O-acetyl group, the 4" position cannot be occupied by an O-iso-valeryl group. Also, disclosed therein is a microbiological process for producing 23-O-demycinosyltylosin by culturing strains of *Streptomyces fradiae* under submerged aerobic fermentation conditions.

U.S. Pat. No. 4,205,163 discloses the preparation of 4"-O-acyl- and 3,4"-di-O-acyltylosin from tylosin or 3-acyltylosin. However, the preparation requires introduction of highly labile 4'''-O-acyl groups such as ethoxycarbonyl, phenoxycarbonyl or haloacetyl which can easily be selectively removed.

Belgian Patent No. 849,847 discloses preparation of 3-O-acyl-4"-O-iso-valeryltylosin by the microbiological acylation of the 3 and 4" hydroxyl groups of tylosin by a mutant organism.

The preparation of 3-O-acetyl-4"-O-iso-valeryl-23-O-demycinosyltylosin directly by mutasynthesis has also been described in Japanese Patent No. 85-16960.

The preparation of DMT by mutasynthesis is described in European Patent No. 96,900.

U.S. Pat. No. 4,396,613 discloses 23-ester derivatives of 23-O-demycinosyltylosin useful as antibiotics and/or as intermediates to antibiotics. The 23-ester derivatives are chemically prepared from 23-O-demycinosyltylosin or from 2'-O-ester derivatives of 23-O-demycinosyltylosin.

U.S. Pat. No. 4,436,729 discloses 23-O-demycinosyltylosin and derivatives thereof which are useful as antibacterials. In addition, there is disclosed a chemical synthesis of 23-O-demycinosyltylosin from suitably protected tylosin derivatives. Selective acylation of 23-O-demycinosyltylosin is also described therein.

U.S. Pat. No. 4,321,361 discloses 23-O-demycinosyltylosin and its 20-dihydro derivatives which are allegedly useful as antibacterial agents active against Gram-positive microorganisms and *Mycoplasma* species. A generic group of esters is disclosed therein and specifically mono esters of the 2'-hyroxyl group are disclosed. The 23-O-demycinosyltylosin is prepared by mutasynthesis, specifically by culturing *Streptomyces fradiae* under submerged aerobic fermentation conditions until a substantial level of antibiotic activity is produced.

Continued extensive use of effective antibacterial agents has given rise to resistant strains of pathogens and to the continuing need for new antibacterial agents, particularly those with high serum and tissue levels.

Increased potency, expanded spectrum of bacterial inhibition, increased in vivo efficacy, and improved pharmaceutical properties e.g., greater oral absorption, higher serum or tissue concentration, longer body half life, and more advantageous rate or route of excretion and rate or pattern of metabolism are some of the goals for improved antibacterials.

There is a need for processes for the preparation of di-, tri- and tetra-O-acyltylosins and di-, tri- and tetra-O-aceyl-23-O-demycinosyltylosins which do not rely on the use of microbiological pathways which do not require the use of 3-O-acetyltylosin as the starting material and which do not require the use of highly labile acyl groups to avoid formation of undesirable side products.

SUMMARY OF THE INVENTION

This invention provides compounds represented by the formula

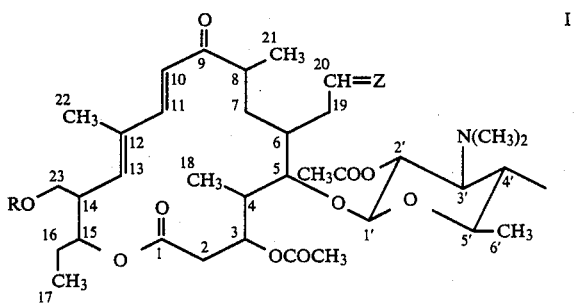

-continued

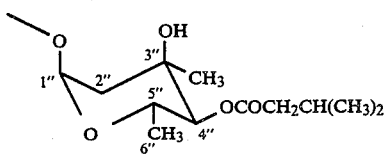

or the pharmaceutically acceptable salts thereof, wherein R is acetyl or H and wherein Z is independently O, =NNH-aralkyl,

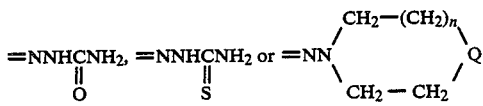

wherein n is 0, 1 or 2 and 0 is independently $CR_1R_2$, $NR_1$, O, S, $SO_2$, $CR_1OR_2$,

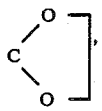

wherein $R_1$ and $R_2$ are independently hydrogen, lower alkyl, aralkyl, X-substituted aralkyl, aryl and X-substituted aryl wherein X is independently halogen, trifluoromethyl, lower alkoxy or lower alkyl carbonyl.

The compounds of this invention are useful as antibacterials against Gram-positive organisms.

This invention also relates to pharmaceutical compositions comprising the compounds of formula I and to methods of treatment, wherein the compounds or pharmaceutical compositions thereof are administered to obtain an antibacterial effect in warm blooded mammals.

The present invention also provides a process for selectively deacylating the 2' and 4'''-positions in 3,2',4'',4'''-tetra-O-acyltylosin or 2',4'',4'''-tri-O-acyltylosin which comprises treating 3,2',4'',4'''-tetra-O-acyltylosin or 2',4'',4'''-triacyltylosin with a deblocking reagent comprising an organic trisubstituted nitrogen base and a lower alkanol to produce 3,4''-di-O-acyltylosin or 4''-O-acyltylosin substantially free of side products.

The present invention further provides a process for selectively acylating 2',4'',4'''-tri-O-acyltylosin which comprises treating 2',4'',4'''-tri-O-acyltylosin with at least about a stoichiometric amount of an acylating agent in the presence of about 0.5 to 1.5 moles of a 4-disubstituted aminopyridine per mole of acylating agent and externally added base to produce 3,2',4'',4'''-tetra-O-acyltylosin substantially free of 3''-O-acyltylosin products.

The present invention still further provides a process for selectively acylating 2',4'''-di-O-acyltylosin which comprises treating 2',4'''-di-O-acyltylosin with about a stoichiometric amount of an acylating agent in the presence of more than about 0.1 to about 1 mole of a 4-disubstituted aminopyridine per mole of acylating agent and externally added base to produce 2',4'',4'''-tri-O-acyltylosin substantially free of 3-O-acyltylosin and/or 3''-O-acyltylosin products.

The present invention further provides a process for preparing 3,2',4''-tri-O-acyl-23-O-demycinosyltylosin and optionally, 3,23,2'4''-tetra-O-acyl-23-O-demycinosyltylosin from tylosin which comprises:

(a) treating tylosin with an acylating agent in an aprotic solvent in the absence of externally added base to produce 2'-O-acyltylosin;

(b) treating the reaction mixture of step (a) with an acylating agent, and a 4-disubstitutedaminopyridine in the presence of externally added base to produce 2',4'''-di-O-acyltylosin;

(c) treating the product of step (b) with about a stoichiometric amount of an acylating agent in the presence of more than about 0.1 to about 1 mole of a 4-substitutedaminopyridine per mole of acylating agent and an externally added base to produce 2',4'',4'''-tri-O-acyltylosin substantially free of 3-O-acyltylosin and/or 3''-O-acyltylosin products;

(d) treating the product of step (c) with at least about a stoichiometric amount of an acylating agent and about 0.5 to about 1.5 moles of a 4-disubstitutedaminopyridine per mole of acylating agent in the presence of externally added base to produce 3,2',4'',4'''-tetra-O-acyltylosin substantially free of 3''-O-acyltylosin products;

(e) selectively deacylating the 2' and 4'''-position of the product of step (d) by treating the product of step (d) with a deblocking reagent comprising an organic tri-substituted nitrogen base and a lower alkanol to produce 3,4''-di-O-acyltylosin substantially free of side products;

(f) treating the product of step (e) with an acylating agent in an aprotic solvent in the absence of externally added base to produce 3,2',4''-O-triacyltylosin;

(g) selectively removing the mycinosyl group at the 23 position to produce 3,2',4''-tri-O-acyl-23-O-demycinosyltylosin; and (h) optionally treating the product of step (g) with an acylating agent in the presence of a 4-disubstitutedaminopyridine and externally added base to produce 3,23,2'4''-tetra-O-acyl-23-O-demycinosyltylosin.

DETAILED DESCRIPTION OF THE INVENTION

We have discovered alternative, highly selective processes for preparing 2',4'',4'''-tri-O-acyltylosin, 3,2',4'',4'''-tetra-O-acyltylosin, 3,4''-di-O-acyltylosin and 4''-O-acyltylosin as well as for producing 3,4''-di-O-acyl-23-O-demycinosyltylosin, 3,2',4''-tri-O-acyl-23-O-demycinosyltylosin, 3,23,2'4''-tetra-O-acyl-23-O-demycinosyltylosin which do not involve mutasynthesis and which do not require the presence of a highly labile acyl group such as trichloroacetyl. The highly selective processes all occur using acylating agents such as for example, acid anhydrides derived from lower alkanoic acids. Thus, the present invention provides a specific reagent and reaction conditions for selectively acylating 2',4'''-di-O-acyltylosin to produce 2',4'',4'''-tri-O-acyltylosin substantially free of 3-O-acyltylosin and/or 3''-O-acyltylosin products and for selectively acylating 2',4'',4'''-tri-O-acyltylosin to produce 3,2',4'',4'''-tetraacyltylosin substantially free of 3''-O-acyltylosin products. The 3,2',4'',4'''-tetracylatedtylosin is then selectively deacylated to remove the acyl groups at the 2'- and 4"-position under conditions that avoid formation of aldol condensation and Michael addition products. Thus, the selective acylation and deacylation process of the present invention avoids formation of the undesirable side products which were formed using prior methods.

The compounds of the present invention have been found to exhibit serum levels that are superior to those of other macrolides such as erythromycin, rosaramicin, tylosin, 3-O-acetyl-4"-O-iso-valeryltylosin or 3-O-acetyl-23-O-demycinosyl-4"-O-iso-valeryltylosin following oral administration to squirrel monkeys. For example, 3,23,2'-tri-O-acetyl-23-O-demycinosyl-4"-O-iso-valeryltylosin also exhibits superior serum levels to those of 3-O-acetyl-4"-O-iso-valeryltylosin, while 3,2'-di-O-acetyl-23-O-demycinosyl-4"-O-iso-valeryltylosin exhibits slightly lower serum levels than those of 3-O-acetyl-4"-O-iso-valeryltylosin when administered orally to squirrel monkeys. 3,23,2'-Tri-O-acetyl-23-O-demycinosyl-4"-O-iso-valeryltylosin has also been found to exhibit higher serum levels when administered intravenously to mice than those of erythromycin, rosaramicin, tylosin, 3-O-acetyl-23-O-demycinosyl-4"-O-iso-valeryltylosin, or 3-O-acetyl-4"-O-iso-valeryltylosin. They have a tylosin-like antibacterial spectrum, but are more potent than tylosin.

In particular, this invention relates to 3,23-di, 3,2'-di- and 3,23,2'-tri-O-acetyl-23-O-demycinosyl-4"-O-iso-valeryltylosins, the hydrazone derivatives thereof and to their pharmaceutically acceptable acid addition salts. The preferred hydrazone derivatives are represented by formula I wherein Z is (4,4-dioxothiomor pholinyl-)imino, ie.,

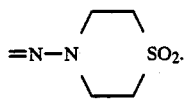

This invention also relates to a pharmaceutical composition comprising the compounds of the invention or their pharmaceutically acceptable acid addition salts, together with a pharmaceutically acceptable carrier.

This invention also relates to methods of treating susceptible infections in warm blooded mammals with said pharmaceutical compositions.

Representative suitable pharmaceutically acceptable acid addition salts include those salts formed by standard reactions with both organic and inorganic acids such as, for example, phosphoric, acetic, succinic, citric, lactic, maleic, fumaric, palmitic, p-glutamic, glutaric, glycolic, tartaric, formic, lauric, stearic, salicylic, sorbic, picric, lactobionic, glucoheptonic, benzoic, cinnamic and like acids.

Preparation of the pharmaceutically acceptable salts of compounds of formula I may be carried out according to conventional procedures for forming salts thereof. Acid addition salts are obtained in the usual manner, for example, by treating with an acid or a suitable anion exchange reagent.

Typical pharmaceutically acceptable carriers suitable for use in the formulations described are exemplified by sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants, ethylene glycol polymers; betacyclodextrin; fatty acids, hydrolyzed cereal solids; water; polyalkylene glycols; gums; and petroleum; as well as other non-toxic compatible fillers, binders, and lubricants commonly used in pharmaceutical formulations. The compositions may also contain preservatives, aerosol propellants and coloring, thickening, suspending, dispensing, emulsifying, wetting, stabilizing and buffering agents.

The term "lower alkyl" as used herein refers to straight and branched-chain alkyl groups of one to six carbons including methyl, ethyl, propyl, butyl, pentyl, hexyl and the corresponding branched-chain isomers thereof.

The term "lower alkoxy" refers to "lower alkyl" groups univalently bonded to divalent oxide and includes inter alia, methoxy, ethoxy and propoxy.

The term "aryl" refers to phenyl and biphenyl.

The term "halogen" refers to fluoro, chloro and bromo, preferably fluoro and chloro.

The term "aralkyl" refers to lower alkyl substituted by aryl (phenyl and biophenyl) including benzyl, phenethyl and O-tolylethyl.

The term "lower alkyl carbonyl" refers to carbonyl groups univalently bonded to "lower alkyl" groups and includes acetyl, propionyl, butyryl and iso-butyryl.

Typically suitable X-substituted aryl groups include p-fluorophenyl, m-chlorophenyl,p-trifluoromethylphenyl, p-ethoxyphenyl, p-acetylphenyl and 3-chloro-4-methoxyphenyl.

Typically suitable X-substituted aralkyl groups include p-fluorobenzyl, m-chlorophenylethyl, and p-trifluoromethylbenzyl.

The deblocking reagents useful in the process aspects of the present invention comprise an organic trisubstituted nitrogen base and a lower alkanol. As used herein, the term "organic trisubstituted nitrogen base" refers to acyclic tertiary amines, pyridine and lower alkyl substituted pyridines and bicyclic teritary amines. Typical suitable acyclic tertiary aliphatic amines include tri(-lower alkyl) amines such as trimethylamine, triethylamine, tri-n-propylamine and dimethyl-sec-butylamine. Triethylamine is the preferred acyclic teritary amine. Typical suitable substituted pyridines include 2-, 3- and 4-methylpyridine. Typical suitable bicyclic tertiary amines include 1,5-diazabicyclo[4.3.0]non-5-ene, hereinafter "DBN" and 1,8-diazabicylo[5.4.0]undec-7-ene, hereinafter "DBU".

The term "lower alkanol" refers to straight and branched-chain alcohols of one to six carbons such as methanol, ethanol, n- and iso-propanol. Methanol is preferred.

As used herein, the term "acylating agent" refers to acid anhydrides and acid halides, especially acid chlorides derived from organic acids such as acetic, propionic, butyric, iso-valeric, oleic, palmitic, stearic, lauric, valeric, benzoic, adamantanecarboxylic, cyclopropanecarboxylic, cyclohexanecarboxylic, cyclohexylpropionic, phenylacetic, mandelic, and 2-thienylacetic acids and alkyl-, aryl- and aralkylsulfonic acids, the aryl and aralkyl acids optionally substituted by halogen, nitro, alkoxy and the like on the aromatic moiety as well as from dicarboxylic acids such as oxalic, succinic, maleic, fumaric, malonic, and phthalic acids. Particularly preferred acylating agents are acid anhydrides of alkanoic acids of 2 to 5 carbon atoms, such as acetic, propionic, n-butyric and iso-valeric, acid anhydrides of aralkanoic acids having from 8 to 10 carbon atoms such as phenylacetic acid anhydride and acid anhydrides of aroic acids having from 7 to 10 carbon atoms, such as benzoic anhydride.

Acylation of the desired hydroxyl groups may be carried out by utilizing known acylation methods for the acylation of common macrolide antibiotics utilizing the novel reaction sequence of the present invention. As the acylating agent, acid halides and acid anhydrides corresponding to the organic acids mentioned above are suitable for use in the process. Acetic anhydride is preferably utilized due to the high yield of product and specificity of reaction. Most preferably, an anhydrous solvent, such as dry acetone or dry dichloromethane is utilized as the reaction medium in the absence of externally added base. Typical reaction temperatures vary from about 10° to about 50° C., with room temperature being preferred. Typical reaction times vary from about 10–70 hours, depending upon the nature of the specific reactants and reaction temperatures employed and the substrate being acylated.

The term "externally added base" refers to teritary organic amine especially tri(lower alkyl)amines such as triethylamine or pyridine.

Acylation of the 2'-hydroxyl

The process begins with the introduction of an acyl group at the 2'-hydroxyl position. It is necessary to block this hydroxyl group prior to the introduction of any acyl group at the 4'" position. In a preferred embodiment of the process of the present invention, where the acyl group to be introduced at the 4'" position is identical to that of the 2'-acyl group, both may be simultaneously introduced, essentially combining the two steps simply by increasing the molar quantities of the acylating agent and adding a base such as pyridine as a catalyst. In another preferred embodiment of the process of the present invention, the 2'-acyl group is introduced in the absence of externally added base to form a reaction mixture. The externally added base, conveniently triethylamine and an increased amount of the acylating agent for acylating the 4'"-hydroxy group are added to the reaction mixture, without isolation to give 2',4'"-di-O-acyltylosin. Selective acylation of the 2'-hydroxyl group may be carried out by the conventional methods known for such acylation of common macrolide antibiotics. In a preferred procedure the acylation is carried out utilizing acetic anhydride in acetone at room temperature for about 24 hours in the absence of externally added base such as pyridine or triethylamine.

Acylation of the 4'"-hydroxyl group

The second acylation step, at the 4'" position, is accomplished utilizing the appropriate acid anhydride in the presence of externally added bases, preferably in the presence of a mixture of pyridine and triethylamine catalytic amounts (0.02 to 0.1 equivalents) of 4-dimethylaminopyridine and dichloromethane at room temperature for about 2–3 days.

Selective Acylation of the 4"-hydroxyl group

Selective acylation of the 4"-hydroxyl group in tylosin is conveniently accomplished by treating 2',4'"-di-O-acyltylosin with about a stoichiometric amount of the appropriate acylating agent in the presence of more than about 0.1 to about 1 mole of a 4-disubstitutedaminopyridine per mole of acylating agent in the presence of externally added base to produce 2',4",4'"-tri-O-acyltylosin substantially free i.e., containing less than about 1% by weight of 3"-O-acyltylosin such as 2',3",4'"-tri-O-acyltylosin and/or 3-O-acyltylosin such as 3,2',4'"-tri-O-acyltylosin.

When the acylation was conducted with more than a stoichiometric amount (e.g., 1.5 times the stoichiometric amount) of acylating agent (per mole of hydroxyl group), acylation of the 3-hydroxyl occurred especially when higher amounts, e.g., 0.8 to 1.0 moles of the 4-disubstitutedaminopyridine per mole of acylating agent were used.

Typical suitable 4-disubstitutedaminopyridines include 4-di(loweralkyl)aminopyridines especially, 4-dimethylaminopyridine, 4-pyrrolidinopyridine and 1,1,3,3-tetra(loweralkyl)-4-(4-pyridyl)guanidine, e.g., 1,1,3,3-tetramethyl-4-(4-pyridyl)guanidine as well as others disclosed by A. Hassner in *Tetrahedron*, Vol. 34, pp 2069–2076 (1978). The preferred 4-disubstitutedaminopyridine is 4-dimethylaminopyridine (DMAP).

Selective acylation at the 4"-position to provide 2',4",4'"-tri-O-acyltylosin is satisfactorily accomplished using about a stoichiometric amount of the appropriate acylating agent, preferably an acid anhydride in the presence of about 0.2 to about 0.5 moles of DMAP per mole of acylating agent and generally about 2.5 moles of externally added base (typically triethylamine or pyridine) per mole of acylating agent and an inert organic solvent.

While acid anhydrides are the preferred acylating agents, acid halides, e.g., acid halides may be used if lower reaction temperatures are employed. The preferred acylating agent of the acid anhydrides is iso-valeric anhydride. Typically suitable externally added bases included tri(loweralkyl)amines, especially triethylamine, pyridine, picoline and piperidine.

Reaction times of about 15–20 hours, normally about 18 hours, are sufficient for complete reaction. Generally, the reaction is carried out in an inert organic solvent such as benzene, toluene, chloroform, dichloromethane, tetrahydrofuran or a mixture thereof. The temperature range is typically between about −10° and about 50° C., but a higher reaction temperature encourages by-product formation. Generally the preferred reaction temperature is between 10° C. and room temperature.

Acylation of the 3"hydroxyl group

Optionally, the 3"-hydroxyl group can also be acylated during the acylation of the 4"-hydroxyl group. The reagents used to acylate the 4"-hydroxyl may be the same as or different than those used to acylate the 3"-hydroxyl, affording a tetra-acyl compound. This 3"-hydroxyl group is a teritary alcohol which reacts only under more severe conditions than those required to acylate the 4"-hydroxyl group. The 3-hydroxyl group must be blocked, preferably by use of the trimethylsilyl ether derivative, prior to the addition of the 3"-acyl group. Generally, conditions must be more severe, i.e., at higher temperatures, i.e., 60°–100° C., and reaction times somewhat longer. Typically, an acyl chloride is utilized as the acylating agent and tribenzylamine as the basic agent. Any nonpolar, organic solvent is suitable for the conduct of the reaction. Of course, when the 3-position is blocked in a synthetic sequence, it must be deblocked at a later stage after the addition of the 3″-acyl group. Typically this is done after the completion of any convenient later stage in the synthetic sequence.

Selective Acylation of the 3-hydroxyl group

Selective acylation of the 3-hydroxyl group in tylosin is usually accomplished by treating 2′,4″,4‴-tri-O-acyltylosin with at least about a stoichiometric amount of the acylating agent in the presence of about 0.5 to about 1.5 moles of a 4-disubstitutedaminopyridine per mole of acylating agent in a dry i.e., water-free inert organic solvent as defined above to produce 3,2′,4″,4‴-tetra-O-acyltylosin substantially free i.e., containing less than about 1% by weight of 3″-O-acyltylosin products such as 3,2′,3″,4″,4‴-penta-O-acyltylosin.

The reaction temperature is typically between −10° and about 50° C., but higher reaction temperatures encourage side-product formation. The preferred acylating agents are acid anhydrides but acid chlorides may be used at low temperatures to avoid side product formation. Use of acid anhydrides at a reaction temperature between 10° and 25° C. is preferred. The preferred 4-disubstitutedaminopyridine is 4-dimethylaminopyridine. Generally, the reaction is complete in 20–30 hours at about 25° C.

Acylation of the 3 position to provide a tetraacyl (or, if the 3″ position has been acylated, a pentaacyl) compound is most satisfactorily accomplished utilizing about 1.5 to about 4 moles of the appropriate acid anhydride with about 0.5 to about 1.5 moles, preferably about 1 mole of 4-dimethylaminopyridine, in the presence of about 2.5 moles of externally added base, e.g., triethylamine per mole of acylating agent and dichloromethane at room temperature for about 20–24 hours.

Selective Removal of 2′ and 4‴-acyl groups

The 2′ and 4‴-acyl groups are selectively removed from tri-O-acyltylosin, e.g., 2′,4″,4‴-tri-O-acyltylosin and from tetra-O-acyltylosin, e.g., 3,2′,4″,4‴-tetra-O-acyltylosin to form 4″-O-acyltylosin and 3,4″-di-O-acyltylosin substantially free of the side products, i.e., the aldol condensation products formed under acidic and basic conditions and Michael addition products formed under basic condition, encountered by use of prior art deblocking methods. By the term "substantially free" as used herein is mean less than about 1% based on desired product. The selective deacylation step is conveniently accomplished by treating the 3,4′,4″,4‴-tetra-O-acyltylosin or 2′,4″,4‴-tri-O-acyltylosin with a deblocking reagent comprising an organic trisubstituted nitrogen base, and a lower alkanol at a temperature in the range of about 0° to 60° C. for about 2½ to 3 days.

The 2′ and 4‴ acyl groups are removed, preferably by utilizing methanol as the lower alkanol and triethylamine as the organic tri-substituted nitrogen base at room temperature (about 20°–30° C.) for about 2.5 days. Generally at least about 2 moles and typically about 5 to about 20 moles of the organic tri-substituted nitrogen base per mole of tetra or tri-acyltylosin are employed. Sufficient lower alkanol is added to form a solution containing about 1.5 to about 3 weight percent of the tri- or tetra-O-acyltylosin per volume of lower alkanol and organic tri-substituted nitrogen base. The resulting 3,4″ di-O-acyl tylosin may then be derivatized, preferably as a hydrazone or it may be used as the starting material for a process for producing 3,4″ di-O-acyl 23-O-demycinosyltylosin (DMT).

Derivitization of the compound to the desired 20-imino compound is accomplished by reaction of the composition with a "1-imino reactant" of the formula

wherein Z is any of the groups defined above except O. Many of the "1-amino reactants" herein utilized are commercially available. Those that must be synthesized may be prepared by one of the procedures found in Biel, et al., J. Org. Chem., 26, 4096 (1961) or Gosl, et al., Org. Syn., Collect. Vol V, 43 (1963). Generally, the reaction is conducted in a non-polar anhydrous organic solvent such as benzene, toluene, chloroform, dichloromethane, tetrahydrofuran or a mixture thereof. Reaction temperatures range from about 0°–50° C., with room temperature being preferred. Reaction times vary from 12 hours to 10 days, depending upon the reactants employed.

Cleavage

The 3,4″ di-O-acyl-23-O-DMT's are prepared by acylating 3,4″-di-O-acyltylosin at the 2′ position and then cleaving the mycinose sugar and the 2′-acyl group. The 3,2′,4″ tri-O-acyl-23-O-DMT compounds may also be formed in the same manner. This is accomplished by reacting the 3,2′,4″- composition with 1-N-ethyl-3-N-(3-dimethylaminopropyl) carbodiimide HCl and dimethyl sulfoxide in pyridine and trifluoroacetic acid for 1½ to 3 days.

A variety of products are produced depending on the reaction conditions: 3,2′,4″-tri-O-acyl-23-O-demycinosyltylosin, 3,2′,4″-tri-O-acyl-4‴-dehydro-4‴-deoxy-4‴-oxotylosin and 3,2′,4″ tri-O-acyl-2‴,3‴,4‴-tridehydro-2‴-demethoxy-4‴-deoxy-4‴-oxotylosin.

The later two compositions will form either 3,4″-di-O-acyl-23-O-demycinosyltylosin and/or 3,2′,4″-tri-O-acyl-23-O-demycinosyltylosin by reaction with triethylamine in methanol under appropriate conditions.

Acylation of these compounds at the 23-O-position may then be accomplished by standard methods, most satisfactorily by utilizing the appropriate anhydride in 4-dimethylaminopyridine, and pyridine or triethylamine and dichloromethane at room temperature for 40–48 hours.

A typical reaction sequence is set forth in Scheme 1.

Scheme 1

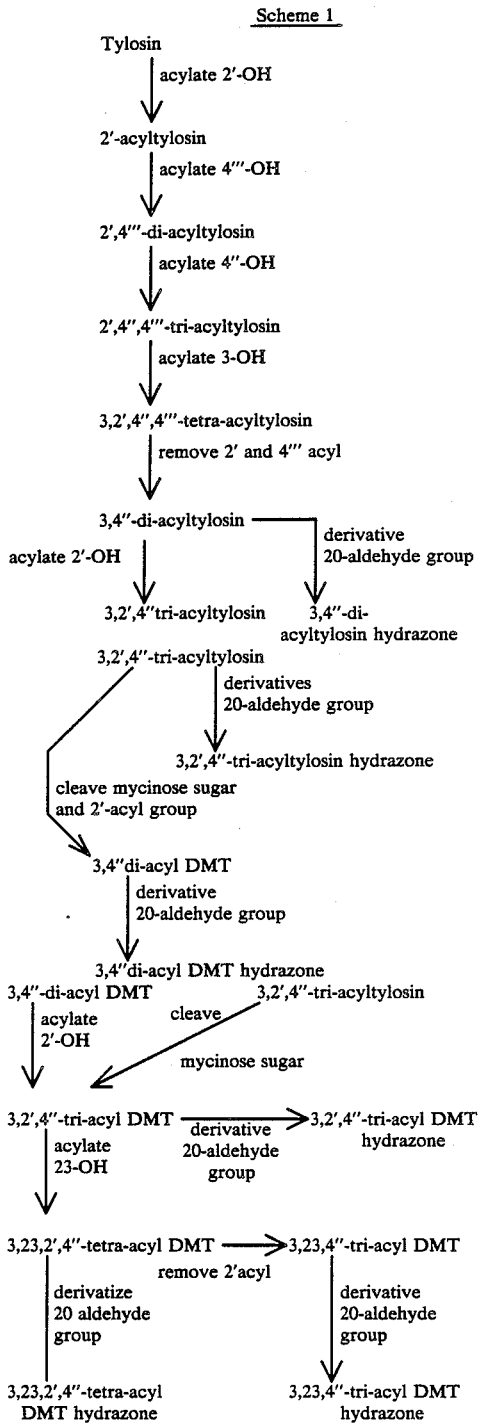

Reaction Scheme II, which follows, summarizes a preferred embodiment of the process of the present invention for the preparation of the ester derivatives of the compounds of this invention.

Scheme II

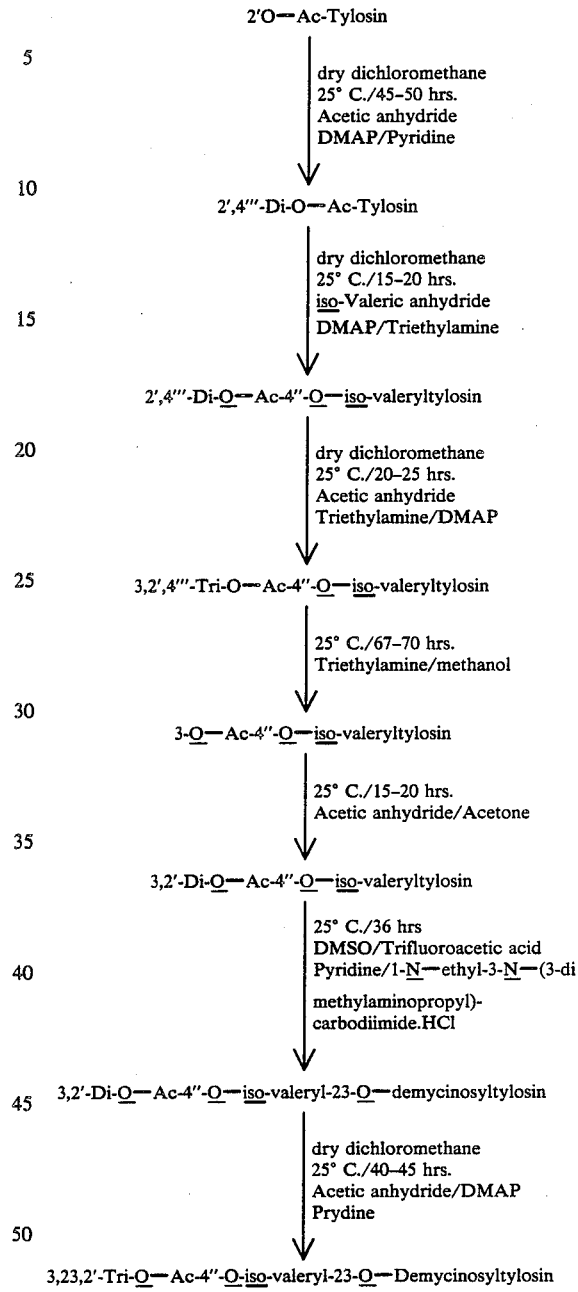

The compounds of this invention may be prepared as shown in the preferred reaction scheme by the reaction of tylosin, which is described in the Merck Index, tenth edition, published by Merck & Co., Inc. (1983) on page 1404, with acetone and acetic anhydride in the absence of externally added base at room temperature about (25° C.) for about 20–25 hours, to give 2'-O-acetyltylosin. The 2'-O-acetyltylosin is then treated with acetic anhydride, 4-dimethylaminopyridine (DMAP) and pyridine in dry dichloromethane at about room temperature for about 45–50 hours, to give 2',4'''-di-O-acetyltylosin.

The 2',4'''-di-O-acetyltylosin is then treated with about a stoichiometric amount of iso-valeric anhydride, about 0.5 moles 4dimethylaminopyridine (DMAP) per mole of iso-valeric anhydride and about 10 moles of triethylamine per mole of iso-valeric anhydride in dry dichloromethane at room temperature for about 15-20 hours to give 2',4'''-di-O-acetyl-4''-O-iso-valeryltylosin. The 2',4'''-di-O-acetyl-4''-O-iso-valeryltylosin is then treated with about 4.30 times the stoichiometric amount of acetic anhydride per mole of tri-acylated tylosin, about 1 mole of 4-dimethylaminopyridine per mole of acetic anhydride, and about 2.6 moles of triethylamine per mole of acetic anhydride in dry dichloromethane at room temperature for about 20-25 hours to give 3,2',4'''-tri-O-acetyl-4''-O-iso-valeryltylosin.

The 3,2',4'''-tri-O-acetyl-4''-O-iso-valeryl-tylosin is then treated with about 15-20 moles of triethylamine per mole of tetra-acyltylosin and sufficient methanol to give about 1.85-2.0 wgt%/volume solution at room temperature for about 65-70 hours to give 3-O-acetyl-4''-O-iso-valeryltylosin. The 3-O-acetyl-4''-O-iso-valeryltylosin is then treated with acetone and acetic anhydride at room temparture for about 15-20 hours to give 3,2'-di-O-acetyl-4''-O-iso-valeryltylosin.

The 3,2'-di-O-acetyl-4''-O-iso-valeryltylosin is then treated with 1-N-ethyl-3-N-(3-dimethylaminopropyl)-carbodiimide·HCl , dimethyl sulfoxide (DMSO), pyridine and trifluoroacetic acid at room temperature for about 35-40 hours to give 3,2'-di-O-acetyl-4''-O-iso-valeryl-23-O-demycinosyltylosin. This product, 3,2'-di-O-acetyl-4''-O-iso-valeryl-23-O-demycinosyltylosin, is then recovered.

The 3,2'-di-O-acetyl-4''-O-iso-valeryl-23-O-demycinosyltylosin is then treated with acetic anhydride, 4-dimethylaminopyridine and pyridine in dry dichloromethane at room temperature for about 40-45 hours to give 3,23,2'-tri-O-acetyl-4''-O-iso-valeryl-23-O-demycinosyltylosin. The latter may also be prepared in a similar manner by treatment of 3-O-acetyl-4''-O-iso-valeryl-23-O-demycinosyltylosin with acetic anhydride, 4-dimethylaminopyridine and pyridine in dry dichloromethane at room temperature for about 40-45 hours.

The compounds of the invention may also be prepared by similar acylation methods to those described above starting from 23-O-demycinosyltylosin.

The compounds of this invention exhibit an antibacterial effect against a wide variety of bacterial species, but are generally more active against strains of Gram-positive bacteria. Exemplary of the bacteria against which the compounds of this invention are active are various strains of *Staphylococci* and *Streptococci*.

The compounds of the invention have a similar spectrum of antibacterial activity to that of the commercial macrolide, tylosin. The compounds are also active against erythromycin resistant strains of *Staphylococci*.

The antibacterial activity of the compounds of this invention is determined by testing against a variety of pathogens using standard antibacterial dilution assays in Mueller-Hinton agar, the activity being expressed as the Minimum Inhibitory Concentration (MIC, mcg./ml., 24 hours). The compounds of this invention inhibit the growth of pathogenic bacteria, especially Gram-positive bacteria. The geometric mean MIC's of the compounds of this invention are in the range of about 0.03 to 4.0.

Most importantly, the compounds of this invention are active antibacterial agents which afford good serum levels at antibacterially effective dosages.

The serum levels of the compounds of this invention were determined in male mice (Carworth CF-1) weighing 18-20 g. each, and squirrel monkeys weighing ca. 1 kg. each. Groups of six mice were given aqueous solutions of the drugs intravenously as single bolus doses of 100 mg./kg., and groups of six monkeys were given the drugs orally as a single dose of 20, or 50 mg./kg. After 1, 3, 5, 10, 20, 30, 45, 60, 90, 120 and 180 min., mice were killed by cutting the jugular vein and the blood allowed to drain into 8 mm. (diameter) tubes which had been standing in a ice water bath. At each time point, blood from the group of mice was pooled. For monkeys, blood samples were taken after 15, 30, 45, 60, 90, 120, 180, 240 and 360 minutes and were not pooled. The samples were left to clot at room temperature for 15 min. After clotting, the samples were centrifuged for 10 min. Serum was removed and put into another test tube in an ice water bath, until antibiotic levels were determined by a cylinder cup method, with either *Bacillus subtilis* ATCC 6633, or *Micrococcus luteus* ATCC 9431 as the test organisms. Stock solutions of each antibacterial were prepared daily in the appropriate vehicle and diluted in homologous serum to prepare a standard curve. Serum samples, diluted where necessary in the appropriate serum, were compared to a standard curve of known potency by standard assay procedures. All assays were done at least twice.

AUCs (areas under the curves) were obtained from serum level vs. time data by the trapezoidal rule.

The results are shown in the following Tables I and II.

TABLE I

| | | Serum levels PO in squirrel monkeys (AUCs, 0-6h.) | | | | | | |
|---|---|---|---|---|---|---|---|---|
| DOSE mg./kg. | CONC.$^a$ mg./ml. | I | II | III | IV | V | VI | VII |
| 20 | 20 | 4.9 | 2.2 | 2.6 | 15.8 | 5.5 | 10.4 | |
| 20 | 10 | 4.8 | | | | | | |
| 20 | 3.5 | 1.5 | | | 7.6$^b$ | | | 13.5$^b$ |
| 50 | 50 | | | 6.6 | 15.6 | | | |
| DOSE mg./kg. | CONC.$^a$ mg./ml. | VIII | IX | X | XI | XII | | |
| 20 | 20 | 7.5 | 2.5 | 4.8 | 4.6 | | | |
| 20 | 10 | | | | | | | |
| 20 | 3.5 | | | | | 3.8 | | |
| 50 | 50 | | | | | | | |

$^a$The vehicle comprises a mixture of 115 ml. of polyethyleneglycol (PEG) 40 castor oil and 1g. of lactic acid USP in 1 litre of distilled water.
$^b$Results were obtained in a crossover experiment.

TABLE II

| | | Serum levels IV in mice (AUCs, 0-3h.) | | | | | |
|---|---|---|---|---|---|---|---|
| DOSE mg./kg. | CONC.$^a$ mg./ml. | I | II | III | IV | V | VII |
| 100 | 10 | 36.1 | 6.6 | 24.2 | 52.4 | 28.3 | 69.4 |
| DOSE mg./kg. | CONC.$^a$ mg./ml. | VIII | IX | X | XI | XII | XIII |
| 100 | 10 | 67.6 | 40.1 | 80.5 | 61.8 | 153.5 | 43.4 |

$^a$The vehicle is the same as described in footnote $^a$ of TABLE I

Key to Compounds in Tables I and II:

I Erythromycin
II Rosaramicin
III Tylosin
IV 3-O-Acetyl-4''-O-iso-valeryltylosin
V 3-O-Acetyl-23-O-demycinosyl-4''-O-isovaleryltylosin
VI 3,2'-Di-O-acetyl-23-O-demycinosyl-4''-O-iso-valeryltylosin VII 3,23,2'-Tri-O-acetyl-23-O-demycinosyl-4"-O-iso-valeryltylosin VIII 3-O-Acetyl-20-deoxo-20-[(4,4-dioxothiomorpholinyl)imino]-4"-O-iso-valeryltylosin IX 3-O-Acetyl-23-O-demycinosyl-20-deoxo-20-[(4,4-dioxothiomorpholinyl)imino]-4"-O-iso-valeryltylosin X 3,2'-Di-O-acetyl-23-O-demycinosyl-20deoxo-20-[(4,4-dioxothiomorpholinyl)imino]-4"-O-iso-valeryltylosin XI 3,23-Di-O-acetyl-23-O-demycinosyl-20-dexo-20-[(4,4-dioxothiomorpholsinyl)imino]-4"-O-iso-valeryltylosin XII 3,23,2'-Tri-O-acetyl-23-O-demycinosyl-20-deoxo-20-[(4,4-dioxothiomorpholinyl)imino]-4"-O-iso-valeryltylosin XIII 3-O-Acetyl-23-O-demycinosyl-20-deoxo-20-[(4,4-dioxothiomorpholinyl)imino]-23-O-phenylacetyl-4"-O-iso-valeryltylosin As is evident from the Tables, the compounds of the present invention exhibit serum levels that are superior to those of other macrolides such as erythromycin, rosaramicin, tylosin, or 3-O-acetyl-23-O-demycinosyl-4"-O-iso-valeryltylosin following oral administration to squirrel monkeys, at comparable doses and concentrations of the drugs in the chosen vehicle. 3,23,2'-Tri-O-acetyl-23-O-demycinosyl-4"-O-iso-valeryltylosin also exhibited superior serum levels to those of 3-O-acetyl-4"-O-iso-valeryltylosin, when administered orally to squirrel monkeys at a dose of 20 mg./kg. and at a concentration of 3.5 mg./ml. in the chosen vehicle. 3,2'-Di-O-acetyl-23-O-demycinosyl-4"-O-iso-valeryltylosin exhibited slightly lower serum levels than those of 3-O-acetyl-4"-O-iso-valeryltylosin when administered orally to squirrel monkeys at a dose of 20 mg./kg. and at a concentration of 20 mg./ml. in the vehicle.

3,23,2'-Tri-O-acetyl-23-O-demycinosyl-4"-O-iso-valeryltylosin and 3,23,2'-tri-O-acetyl-23-O-demycinosyl-20-deoxo-20-[(4,4-dioxothiomorpholinyl)imino]-4"-O-iso-valeryltylosin and have also been found to exhibit serum levels that are superior to those of other macrolides such as erythromycin, rosaramicin, tylosin, 3-O-acetyl-4"-O-iso-valeryltylosin, or 3-O-acetyl-23-O-demycinosyl-4"-O-iso-valeryltylosin, when administered intravenously to mice at a dose of 100 mg./kg. and at a concentration of 10 mg./ml. in the vehicle.

Of course, it should be appreciated that the amount of antibacterial derivative used will vary dependent upon the particular compound used, the mode of application, the route of administration and the like. The factors which modify the action of the drug will be taken into account by the skilled practitioner. For example, age, body weight, sex, diet, time of administration, route of administration, rate of metabolism or excretion, other drugs being administered, severity of infection all play a role in the quantum and frequency of administration of the derivatives disclosed herein. However, the compounds of this invention are generally administered in the range of from about 1 to about 500 mg/kg/day, preferably 5 to 50 mg/kg/day in divided doses.

The following examples illustrate the preparation of the compounds of this invention and pharmaceutical composition of the compounds.

EXAMPLE 1

3-O-Acetyl-4"-O-iso-valeryltylosin from Tylosin (i) 2'-O-Acetyltylosin from tylosin.

Tylosin (101.1 g, 0.1104 mole) was dissolved in dry acetone (1.2 l.) and acetic anhydride (21 ml, 0.223 mole) was added. The mixture was allowed to stand under dry argon at 25° C. for 23h. The solution was evaporated to dryness and the residue was taken up in dichloromethane and washed with water, the pH being adjusted to 10. The organic layer was dried (MgSO$_4$), filtered and evaporated to dryness. The residue was azeotroped with toluene (3×500 ml.) to afford 2'-O-acetyltylosin (105.7 g., 100%) as a colorless amorphous solid that was used directly without further purification.

(ii) 2',4'''-Di-O-acetyltylosin from 2'-O-acetyltylosin.

2'-O-Acetyltylosin (121.8 g, 0.127 mole), 4-dimethylaminopyridine (3.11 g, 0.0255 mole) and dry pyridine (15.47 ml, 0.192 moles) were dissolved in dry dichloromethane (1.5 l.) and acetic anhydride (7.18 ml, 7.77 g, 0.0762 mole) was added. The mixture was allowed to stand under dry argon at 25° C. for 19h. Additional acetic anhydride (3.59 ml, 0.0381 mole) was added and the reaction was allowed to continue for a total of 47h. The solution was diluted with dichloromethane and washed with water, the pH being adjusted to 10. The organic layer was dried (MgSO$_4$), filtered and evaporated to dryness. The residue was purified by preparative hplc using a Waters prep 500 (2 silica gel cartridges/40 g. of substrate) and 25% increasing to 50% acetone in hexane as the eluant to give 2',4'''-di-O-acetyltylosin (53.9 g., 49%) as a colorless amorphous solid, (Found: C,60.10; H,8.16; N,1.26. $C_{50}H_{80}NO_{19}$ requires: C,60.10; H,8.07; N 1.40%), $[\alpha]_D^{26}$ −49.8° (CHCl$_3$), λmax (CF$_3$CH$_2$OH) 285 nm ( 21,608), λmax (CDCl$_3$) 3490, 1740, 1680, 1600, 1240, 1168, 1058, cm.$^{-1}$, $\delta_H$ (CDCl$_3$) 1.81 (3H, d, $J_{12-CH_3,13}$ 1Hz, 12—CH$_3$), 2.08 (3H, s, 2'—OCOCH$_3$), 2.13 (3H, s, 4'''-OCH$_3$), 3.54 (3H, s, 3'''-OCH$_3$), 4.30 (1H, d, $J_{1''ax,2'ax}$ 8Hz, H$_1$,ax), 4.48 (1H, dd, $J_{1''ax,2''ax}$ 10 Hz, $J_{1''ax,2''eq}$ 2.5Hz, H$_{1''ax}$), 4.67 (1H, d, $J_{1'''ax,2'''ax}$ 8Hz, H$_{1'''ax}$), 5.95 (1H, dq, $J_{12-CH_3,13}$ 1Hz, $J_{13,14}$ 10Hz, H$_{13}$), 6.33 (1H, d, $J_{10,11}$ 15.5Hz, H$_{10}$), 7.37 (1H, d, $J_{10,11}$ 15.5Hz, H$_{11}$) and 9.70 (1H, s, H$_{20}$).

The fractions that were slightly less polar than the diacetate afforded 2',4''',4'''-tri-O-acetyltylosin (3.6 g., 3%) as a colorless amorphous solid, (Found: C,59.93; H,8.00; N,1.01. $C_{52}H_{82}NO_{20}$ requires: C,59.93; H,7.87; N,1.34%), m/z 1042 (MH$^+$), $[\alpha]_D^{26}$ −45.8° (CHCl$_3$), λmax (CF$_3$CH$_2$OH) 285 nm ( 21,675), λmax (CDCl$_3$) 3490; 1638, 1675, 1590, 1240, 1160, 1050 cm.$^{-1}$, $\delta_H$ (CDCl$_3$) 1.80 (3H, d, $J_{12-CH_3,13}$ 1Hz, 12—CH$_3$), 2.08 (3H, s, 2'—OCOCH$_3$), 2.12 (3H, s, 4'''—OCOCH$_3$), 2.16 (3H, s, 4''—OCOCH$_3$), 2.42 (6H, s, 3'-N(CH$_3$)$_2$), 3.49 (3H, s, 2'''—OCH$_3$), 3.53 (3H, s, 3'''—OCH$_3$), 5.93 (1H, dg, $J_{12-CH_3,13}$ 1Hz, $J_{13,14}$ 10Hz, H$_{13}$), 6.32 (1H, d, $J_{10,11}$ 15.5Hz, H$_{10}$), 7.35 (1H, d, $J_{10,11}$ 15.5Hz, H$_{11}$) and 9.69 (1H, s, H$_{20}$).

The most polar fractions from the column afforded unreacted 2'-O-acetyltylosin (16.8 g., 16%).

(iii) 2',4'''Di-O-acetyl-4"-O-iso-valeryltylosin from 2',4'''-di-O-acetyltylosin.

2',4'''-Di-O-acetyltylosin (53.8 g, 0.0534 mole), 4-dimethylaminopyridine (3.28 g, 0.0268 mole) and triethylamine (54.4 g, 0.539 mole) were dissolved in dry dichloromethane (1.08 l.) and iso-valeric anhydride (10.01 g, 0.0537 mole) was added. The mixture was allowed to remain at 25° C. under dry argon for 18h. The solution was diluted with dichloromethane and washed with water, the pH being adjusted to 10. The organic layer was dried (MgSO$_4$), filtered and evaporated to dryness. The residue was purified by preparative hplc on a Waters prep 500 (2 silica gel cartridges) using 17% acetone in hexane as the eluant to give 2',4'''-di-O-acetyl-4''-O-iso-valeryltylosin (28.5 g., 49%) as a colorless amorphous solid, (Found: C,60.11; H,7.93; N,1.05. C$_{55}$H$_{91}$NO$_{20}$ requires: C,60.14; H,8.35; N,1.28%), m/z 1098 (MH+), [α]$_D^{26}$ −47.2° (CHCl$_3$), λmax (CF$_3$CH$_2$OH) 285 nm ( 20,483), λmax (CDCl$_3$) 3500; 1745, 1730, 1680, 1595, 1245, 1170, 1060, 1040 cm.$^{-1}$, δ$_H$ (CDCl$_3$) 0.97 (6H, d, J, 7Hz, 4''—O—COCH$_2$CH(CH$_3$)$_2$), 1.78 (3H, d, J$_{12-CH_3,13}$ 1Hz, 12—CH$_3$), 2.07 (3H, s, 2'—OCOCH$_3$), 2.10 (3H, s, 4'''—OCOCH$_3$), 2.40 (6H, s, 3'—N(CH$_3$)$_2$), 3.48 (3H, s, 2'''—OCH$_3$), 3.52 (3H, s, 3'''—OCH$_3$), 4.64 (1H, d, J$_{1'''ax,2'''ax}$ 9Hz, H$_{1'''ax}$), 5.94 (1H, dq, J$_{12-CH_3,13}$ 1Hz, J$_{13,14}$ 10Hz, H$_{13}$), 6.30 (1H, d, J$_{10,11}$ 15.5Hz, H$_{10}$), 7.34 (1H, d, J$_{10,11}$ 15.5Hz, H$_{11}$) and 9.68 (1H, s, H$_{20}$).

The unreacted starting material was recycled twice to give a total yield of valerate (35.6 g., 61%). A small amount of unreacted starting material (1.74 g., 3%) remained. No tetra-O-acetyltylosin, i.e., 2',4'''-di-acetyl-3,4''-di-O-iso-valeryltylosin or 2',4'''-di-O-acetyl-3'',4''-di-O-iso-valeryltylosin was detected by tlc.

(iv) 3,2',4'''-Tri-O-acetyl-4''-O-iso-valeryltylosin from 2',4'''-di-O-acetyl-4''-O-iso-valeryltylosin.

2',4'''-Di-O-acetyl-4''-O-iso-valeryltylosin (35.8 g, 0.0326 mole) 4-dimethylaminopyridine (16.1 g, 0.132 mole) and triethylamine (25.1 ml, 0.181 mole) were dissolved in dry dichloromethane (1.2 l) and acetic anhydride (12.3 ml, 13.31 g, 0.1305 mole) was added. The mixture was allowed to remain at 25° C. under dry argon for 21 hours. The mixture was diluted with dichloromethane and washed with water, the pH being adjusted to 10. The organic layer was dried (MgSO$_4$), filtered and evaporated to dryness. The residue was purified by preparative hplc on a Waters Prep 500 (one silica gel cartridge/10 g substrate) using 17% acetone in hexane as the eluant to give 3,2',4'''-tri-O-acetyl-4''-O-iso-valeryltylosin (30.8 g, 82%) as a colourless amorphous solid, (Found: C, 60.93; H, 8.03; N, 1.46 . C$_{57}$H$_{93}$NO$_{21}$ requires: C, 60.67; H, 8.31; N, 1.24%), m/z 1128 (MH+), [α]$_D^{26}$ −36.2° (CHCl$_3$), λmax (CF$_3$CH$_2$OH) 283 nm ( 21,423), λmax (CDCl$_3$) 3500, 1740, 1680, 1595, 1245, 1170, 1060, 1035 cm$^{-1}$, δ$_H$ (CDCl$_3$) 0.98 (6H, d, J6Hz, 4''-OCOCH$_2$CH(CH$_3$)$_2$), 1.80 (3H, d, J$_{12,CH_3,13}$ 1Hz, 12—CH$_3$), 2.07 (3H, s, 2'—OCOCH$_3$), 2.11 (3H, s, 3—OCOCH$_3$), 2.12 (3H, s, 4'''—OCOCH$_3$), 2.41 (6H, s, 3'—N(CH$_3$)$_2$), 3.45 (3H, s, 2'''—OCH$_3$), 3.51 (3H, s, 3'''—OCH$_3$), 5.94 (1H, dq, J$_{12-CH_3,13}$ 1Hz, J$_{13,14}$ 10Hz, H$_{13}$), 6.31 (1H, d, J$_{10,11}$ 15.5Hz, H$_{10}$), 7.41 (1H, d, J$_{10,11}$ 15.5Hz, H$_{11}$) and 9.62 (H, s, H$_{20}$). No 3''-O-acyltylosin products were detected by tlc.

(v) 3-O-Acetyl-4''-O-iso-valeryltylosin from 3,2',4'''-tri-O-acetyl-4''-O-iso-valeryltylosin.

3,2',4'''-Tri-O-acetyl-4''-O-iso-valeryltylosin (1.85 g, 0.00164 mole) and triethylamine (3.5 ml, 2.54 g, 0.0253 mole) were dissolved in methanol (200 ml) and the solution was allowed to stand at 25° C. for 67 hours. The mixture was evaporated to dryness and the residue was chromatographed on a silica gel column (30×2 cm) using 25% acetone in hexane as the eluant to give 3-O-acetyl-4''-O-iso-valeryltylosin (867.5 mg, 51%), as well as a partially deacylated forecut. The latter (783 mg) was dissolved in methanol (50 ml) containing triethylamine (1 ml) and allowed to remain at 25° C. for 66 hours. The product was isolated as above to give a total yield of 3-O-acetyl-4''-O-iso-valeryltylosin (1.47 g, 86%) as a colourless amorphous solid, (Found: C, 60.70; H, 8.39; N, 1.26 . C$_{53}$H$_{87}$NO$_{19}$ requires: C, 61.07; H, 8.41; N, 1.34%), m/z 1042 (MH+), [α]$_D^{26}$ −38.0° (CHCl$_3$), λmax (CH$_3$OH) 282 nm ( 21,611), λmax (CDCl$_3$) 3500, 1725, 1690, 1598, 1240, 1168, 1055, cm.$^{-1}$, δ$_H$ (CDCl$_3$) 0.98 (6H, d, J6Hz, 4''—O—COCH$_2$CH(CH$_3$)$_2$), 1.81 (3H, d, J$_{12-CH_3,13}$ 1Hz, 12—CH$_3$), 2.11 (3H, s, 3—OCOCH$_3$), 2.53 (6H, s, 3'—N(CH$_3$)$_2$), 3.47 (3H, s, 2'''—OCH$_3$), 3.62 (3H, s, 3'''—OCH$_3$), 4.18 (1H, d, J$_{1'ax,2'ax}$ 8Hz, H$_{1'ax}$), 4.67 (1H, d, J$_{1'''ax,2'''ax}$ 8Hz, H$_1'''$ax), 5.98 (1H, dq, J$_{12-CH_3,13}$ 1Hz, J$_{13,14}$ 10Hz, H$_{13}$), 6.29 (1H, d, J$_{10,11}$ 15.5Hz, H$_{10}$), 7.43 (1H, d, J$_{10,11}$ 15.5Hz, H$_{11}$) and 9.64 (H, s, H$_{20}$). No aldol or Michael addition products were detected by tlc.

(vi) 3-O-Acetyl-20-deoxo-20-[(4,4-dioxothiomorpholinyl)imino]-4''-O-iso-valeryltylosin from 3-O-acetyl-4''-O-iso-valeryltylosin.

3-O-Acetyl-4''-O-iso-valeryltylosin (495 mg) and 1-N-amino-4,4-dioxothiomorpholine (71.3 mg) were dissolved in ethanol (20 ml) and the mixture was allowed to stand at 25° C. under dry argon for 20 hours. The solution was evaporated to dryness and the residue was chromatographed on a silica gel column (60 ×2 cm) using 25% acetone in hexane as the eluant to give 3-O-acetyl-20-deoxo-20-[(4,4-dioxothiomorpholinyl)imino]-4''-O-iso-valeryltylosin (437 mg, 79%) as a colourless amorphous solid, (Found: C, 57.98; H, 7.95; N, 3.38 . C$_{57}$H$_{95}$NO$_3$O$_{20}$S requires: C, 58.29; H, 8.15; N, 3.58%), m/z 1174 (MH+), [α]$_D^{26}$ −87.3° (CHCl$_3$), max (CF$_3$CH$_2$OH) 235 nm ( 7,620), 285 nm ( 21,771), max (CDCl$_3$) 3500, 1738, 1675, 1595, 1195, 1165, 1130, 1060 cm.$^{-1}$, δ$_H$ (CDCl$_3$) 0.92 (3H, t, J$_{16,17-CH_3}$ 7Hz, 17—CH$_3$), 0.97 (6H, d, J7Hz, 4''—O—COCH$_2$CH(CH$_3$)$_2$), 1.78 (3H, d, J$_{12-CH_3,13}$ 1Hz, 12—CH$_3$), 2.01 (3H, s, 3—OCOCH$_3$), 2.52 (6H, s, 3'—N(CH$_3$)$_2$), 3.47 (3H, s, 2'''—OCH$_3$), 3.62 (3H, s, 3'''—OCH$_3$), 4.18 (1H, d, J$_{1'ax,2'ax}$ 7.5Hz, H$_{1'ax}$), 4.55 (1H, d, J$_{1'''ax,2'''ax}$ 8Hz, H$_{1'''ax}$), 5.95 (1H, dq, J$_{12-CH_3,13}$ 1Hz, J$_{13,14}$ 10.5Hz, H$_{13}$), 6.26 (1H, d, J$_{10,11}$ 15.5Hz, H$_{10}$), 6.98 (1H, dd, J$_{19,20}$=J$_{19',20}$=4Hz, H$_{20}$) and 7.41 (1H, d, J$_{10,11}$ 15.5Hz, H$_{11}$).

EXAMPLE 2

23-O-Demycinosyl derivatives of 3-O-acetyl-4''-O-iso-valeryltylosin (i) 3,2'-Di-O-acetyl-4''-O-sio-valeryltylosin.

3-O-Acetyl-4''-O-iso-valeryltylosin (5 g, 0.0048 mole) was dissolved in dry acetone (280 ml) and acetic anhydride (2.56 ml, 0.0272 mole) was added. The mixture was allowed to remain under dry argon at 25° C. for 18 hours. The solution was evaporated to dryness and the residue was taken up in dichloromethane and washed with water, the pH being adjusted to 10. The organic layer was dried (MgSO$_4$), filtered and evaporated to dryness. The residue was chromatographed on a silica gel column (30×6 cm) using 15% acetone in hexane as the eluant to give 3,2'-di-O-acetyl-4"-O-iso-valeryltylosin (4.54 g, 87%) as a colorless amorphous solid, (Found: C, 59.59; H, 8.34; N, 1.12 . $C_{55}H_{89}NO_{20} . 0.2$ $CHCl_3$ requires: C, 59.61; H, 8.10; N, 1.26%), m/z 1084 (MH+), $[\alpha]_D^{26}$ −50.9° ($CHCl_3$), λmax ($CF_3CH_2OH$) 285 nm ( 19,983), λmax ($CDCl_3$) 3495, 1730, 1680, 1592, 1238, 1166, 1058, 1027 cm.$^{-1}$, $\delta_H$ ($CDCl_3$) 0.96 (6H, d, J6Hz, 4"-$OCOCH_2CH(CH_3)_2$), 1.78 (3H, d, $J_{12-CH_3,13}$ 1Hz, 12-$CH_3$), 2.03 (3H, s, 3—$OCOCH_3$), 2.07 (3H, s, 2'—$OCOCH_3$), 2.39 (6H, s, 3'—$N(CH_3)_2$), 3.44 (3H, s, 2'—$OCH_3$), 3.58 (3H, s, 3'''—$OCH_3$), 5.89 (1H, dq, $J_{12-CH_3,13}$ 1Hz, $J_{13,14}$ 10Hz, $H_{13}$), 6.23 (1H, d, $J_{10,11}$ 15.5Hz, $H_{10}$), 7.36 (1H, d, $J_{10,11}$ 15.5Hz, $H_{11}$), and 9.60 (1H, s, $H_{20}$).

(ii) Oxidation of 3,2'-di-O-acetyl-4"-O-iso-valeryltylosin.

(a) 1-N-Ethyl-3-N-(3-dimethylaminopropyl)-carbodiimide hydrochloride (1.06 g, 0.0056 mole) was dissolved in dry dimethylsulfoxide (12.5 ml) and 3,2'-di-O-acetyl-4"-O-iso-valeryltylosin (500 mg, 0.0005 mole) was added. The solution was stirred under argon at 25° C. and a mixture of pyridine (0.149 ml, 0.0019 mole) and trifluoroacetic acid (0.0709 ml, 0.0010 mole) in dry dimethylsulfoxide (2.2 ml) was added. The mixture was stirred at 25° C. for 18 hours. The solution was evaporated to dryness under high vacuum and the residue was taken up in dichloromethane and washed with water, the pH being adjusted to 8.6. The dichloromethane extract was dried ($MgSO_4$), filtered and evaporated to dryness. The residue was chromatographed on a silica gel column (30×2 cm) using a rapid elution with 13% acetone in chloroform as the eluant to afford 3,2'-di-O-acetyl-4'''-dehydro-4'''-deoxy-4'''-oxo-4"-O-iso-valeryltylosin (307 mg, 61%) as a colourless amorphous solid, (Found: C, 60.02; H, 8.67; N, 1.07 . $C_{55}H_{87}NO_{20} . 0.1$ $CHCl_3$ requires: C, 60.37; H, 8.02; N, 1.28%), m/z 1082 (MH+), $[\alpha]_D^{26}$ −38.8° ($CHCl_3$), λmax ($CF_3CH_2OH$) 284 nm ( 22,098), λmax ($CDCl_3$) 3680, 3500, 1734, 1675, 1594, 1238, 1165, 1060 1027 cm.$^{-1}$, $\delta_H$ ($CDCl_3$) 0.94 (3H, t, $J_{16,17-CH_3}$ 6.5Hz, 17-$CH_3$), 0.99 (6H, d, J6.5Hz 4"—$OCOCH_2(CH_3)_2$), 1.13 (3H, s, 3'''—$CH_3$), 1.15 (3H, d, J6.5Hz,$CH_3$), 1.22 (3H, d, J6.5Hz, $CH_3$), 1.24 (3H, d, J6.5Hz, $CH_3$), 1.35 (3H, d, $J_{5''',6'''-CH_3}$ 6.5Hz, 6'''—$CH_3$), 1.84 (3H, d, $J_{12-CH_3,13}$ 1Hz, 12—$CH_3$), 2.10 (3H, s, 2'—$OCOCH_3$), 2.15 (3H, s, 3—$OCOCH_3$), 2.41 (6H, s, 3'—$N(CH_3)_2$), 3.52 (3H, s, 2'''—$OCH_3$), 3.60 (3H, s, 3'''—$OCH_3$), 4.26 (1H, d, $J_{1'ax,2'ax}$ 8Hz, $H_{1'ax}$), 4.63 (1H, d, $J_{1'''ax,2''ax}$ 8Hz, $H_{1'''ax}$), 5.93 (1H, dq, $J_{13,14}$ 10Hz, $J_{12-CH_3,13}$ 1Hz, $H_{13}$), 6.33 (1H, d, $J_{10,11}$ 16Hz, $H_{10}$), 7.43 (1H, d, $J_{10,11}$ 16Hz, $H_{11}$) and 9.63 (1H, s, $H_{20}$).

(b) 1-N-Ethyl-3-N-(3-dimethylaminopropyl) carbodiimide hydrochloride (1.59 g, 0.0083 mole) was dissolved in dry dimethylsulfoxide (20 ml, 0.0007 mole) and 3,2'-di-O-acetyl-4"-O-iso-valeryltylosin (750 mg) was added. The solution was stirred under argon at 25° C. and a mixture of pyridine (0.2235 ml, 0.0028 mole) and trifluoroacetic acid (0.1064 ml, 0.0014 mole) in dry dimethylsulfoxide (1 ml) was added. The mixture was stirred at 25° C. for 19 hours. The solution was evaporated to dryness under high vacuum and the residue was taken up in dichloromethane and washed with water, the pH being adjusted to 9.7. The dichloromethane extract was dried ($MgSO_4$), filtered and evaporated to dryness. The residue was chromatographed on a silica gel column (30×2 cm) using first chloroform (500 ml) and the 13% acetone in chloroform as the eluant. The product was rechromatographed on a silica gel column (30×2 cm) using 8% acetone in chloroform as the eluant to give 3,2'-di-O-acetyl-2''',3''',4'''-tridehydro-2'''-demethoxy-4'''-deoxy-4'''-oxo-4"-O-iso-valeryltylosin (267 mg, 35%) as a colourless amorphous solid, (Found: C, 59.64; H, 7.43; N, 1.19 . $C_{54}H_{83}NO_{19} . 0.3$ $CHCl_3$ requires: C, 59.72; H, 7.70; N, 1.29%), m/z 1051 (MH+), $[\alpha]_D^{26}$ −29.7° ($CHCl_3$) λmax ($CF_3CH_2OH$) 283 nm ( 21,850), λmax ($CDCl_3$) 3680, 3498, 1735, 1678, 1628, 1596, 1238, 1167, 1060, 1028 cm.$^{-1}$, $\delta_H$ ($CDCl_3$) 0.94 (3H, t, $J_{16,17-CH_3}$ 7Hz, 17-$CH_3$), 0.99 (6H, d, J7Hz 4"-$OCOCH_2CH(CH_3)_2$), 1.49 (3H, d, $J_{5'''ax,6'''-CH_3}$ 7Hz, 6'''—$CH_3$), 1.83 (3H, d, $J_{12-CH_3,13}$ 1Hz, 12—$CH_3$), 2.07 (3H, s, 2'—$OCOCH_3$), 2.13 (3H, s, 3—$OCOCH_3$), 2.40 (6H, s, 3'—$N(CH_3)_2$), 3.64 (3H, s, 3'''—$OCH_3$), 4.20 (1H, d, $J_{1'ax,2'ax}$ 8Hz, $H_{1'ax}$), 5.41 (1H, dd, $J_{1'''ax,5'''ax}$ 1.5Hz, $J_{1'''ax,2'''ax}$ 2Hz, $H_{1'''ax}$), 5.68 (1H, d, $J_{1'''ax,2'''ax}$ 2Hz, $H_{2'''}$), 6.88 (1H, dq, $J_{12-CH_3,13}$ 1Hz, $J_{13,14}$ 10Hz, $H_{13}$), 6.30 (1H, d, $J_{10,11}$ 15.5Hz, $H_{10}$), 7.38 (1H, d, $J_{10,11}$ 15.5Hz, $H_{11}$) and 9.60 (1H, s, $H_{20}$), and 3,2'-di-O-acetyl-23-O-demycinosyl-4"-O-iso valeryltylosin (159 mg, 25%) as a colourless amorphous solid, (Found: C, 56.38; H, 6.99; N, 1.22 . $C_{47}H_{75}NO_{16} . 0.8CHCl_3$ requires: C, 56.24; H, 7.52; N, 1.39%), m/z 910 (MH+), $[\alpha]_D^{26}$ −40.6° ($CHCl_3$), λmax ($CF_3CH_2OH$) 284 nm ( 16,890), λmax ($CDCl_3$) 3490, 1737, 1680, 1595, 1238, 1167, 1059, 1029 cm.$^{-1}$, $\delta_H$ ($CDCl_3$) 0.93 (3H, t, $J_{16,17-CH_3}$ 7Hz, 17—$CH_3$), 0.98 (6H, d, J7Hz, 4"—$OCOCH_2CH(CH_3)_2$), 1.13 (3H, s, 3'''—$CH_3$), 1.14 (3H, d, J7Hz, $CH_3$), 1.22 (3H, d, J7Hz, $CH_3$), 1.86 (3H, d, $J_{12-CH_3,13}$ 1Hz, 12—$CH_3$), 2.07 (3H, s, 2'—$OCOCH_3$), 2.14 (3H, s, 3—$OCOCH_3$), 2.42 (6H, s, 3'—$N(CH_3)_2$), 4.27 (1H, d, $J_{1'ax,2'ax}$ 8Hz, $H_{1'ax}$), 5.92 (1H, dq, $J_{12-CH_3,13}$ 1Hz, $J_{13,14}$ 10Hz, $H_{13}$), 6.34 (1H, d, $J_{10,11}$ 15.5Hz, $H_{10}$), 7.43 (1H, d, $J_{10,11}$ 15.5Hz, $H_{11}$) and 9.63 (H, s, $H_{20}$).

(iii) 3,2'-Di-O-acetyl-23-O-demycinosyl-4"-O-iso-valeryltylosin.

(a) 3,2'-Di-O-acetyl-4'''-dehydro-4'''-deoxy-4'''-oxo-4"-O-iso-valeryltylosin (2 mg) and Baker silica gel (60–200 mesh) (200 mg) were added to 8% acetone in chloroform (1 ml) and the mixture was stirred at 25° C. for 42 hours. The silica gel was filtered off, washed with acetone and the combined filtrates were evaporated to dryness to give 3,2'-di-O-acetyl-2''',3''',4'''-tridehydro-2'''-demethoxy-4'''-deoxy-4'''-oxo-4"-O-iso-valeryltylosin (40%), 3,2'-Di-O-acetyl-4'''-dehydro-4'''-deoxy-4'''-oxo-4"-O-iso-valeryltylosin (40%) and 3,2'-di-O-acetyl-23-O-demycinosyl-4"-O-iso-valeryltylosin (10%), all of which were identical with authentic samples on tlc (40% acetone in chloroform as eluant).

(b) 3,2'-Di-O-acetyl-4'''-dehydro-4'''-deoxy-4'''-oxo-4"-O-iso-valeryltylosin (5 mg) was dissolved in a 1.3% solution of triethylamine in methanol (0.013 ml/1 ml) and the mixture was stirred at 25° C. for 20 hours. The solution was evaporated to dryness to give 3,2'-di-O-acetyl-23-O-demycinosyl-4"-O-iso-valeryltylosin (50%) and 3-O-acetyl-23-O-demycinosyl-4"-O-iso-valeryltylosin (45%), which were identical with authentic samples on tlc (40% acetone in chloroform as eluant).

(c) 3,2'-Di-O-acetyl-2''',3''',4'''-tridehydro-2'''-demethoxy-4'''-deoxy-4'''-oxo-4"-O-iso-valeryltylosin (2 mg) and Baker silica gel (60–200 mesh) (200 mg) were added to 8% acetone in chloroform (1 ml) and the mixture was stirred at 25° C. for 42 hours. The silica gel was filtered off, washed with acetone and the combined filtrates were evaporated to dryness to give 3,2'-di-O-acetyl- 2''',3''',4'''-tridehydro-2'''-demethoxy-4'''-deoxy-4'''-oxo-4''-O-iso-valeryltylosin (75%) and 3,2'-di-O-acetyl-23-O-demycinosyl-4''-O-iso-valeryltylosin (20%), both of which were identical with authentic samples on tlc (40% acetone in chloroform as eluant).

(d) 3,2'-Di-O-acetyl-2''',3''',4'''-tridehydro-2'''-demethoxy-4'''-deoxy-4'''-oxo-4''-O-iso-valeryltylosin (104 mg) was dissolved in a 1.73% solution of triethylamine in methanol (0.277 ml/16 ml) and the mixture was allowed to remain at 25° C. for 18 hours. The solution was evaporated to dryness and the residue was chromatographed on a silica gel column (30×2 cm) using 15% acetone in chloroform as the eluant to give 3,2'-di-O-acetyl-23-O-demycinosyl-4''-O-iso-valeryltylosin (24 mg, 26%) and 3-O-acetyl-23-O-demycinosyl-4''-O-iso-valeryltylosin (50 mg, 58%) as a colorless amorphous solid, (Found: C, 61.46; H, 8.15; N, 2.09. $C_{45}H_{73}NO_{15}$ . 0.1 $CHCl_3$ requires: C, 61.42; H, 8.36; N, 1.59%), m/z 868 (MH+), $[\alpha]_D^{26}$ −30.7° ($CHCl_3$), λmax ($CH_3OH$) 282 nm ( 20,056), λmax ($CDCl_3$) 3590, 3480, 1729, 1678, 1596, 1240, 1182, 1173, 1050, 1025 cm.$^{-1}$, $\delta_H$ ($CDCl_3$) 0.93 (3H, t, $J_{16,17-CH_3}$ 7Hz, 17—$CH_3$), 0.98 (6H, d, J7Hz, 4''—$OCOCH_2CH(CH_3)_2$), 1.07 (3H, d, J7Hz,$CH_3$) 1.11 (3H, s, 3''—$CH_3$), 1.13 (3H, d, J7Hz, $CH_3$), 1.22 (3H, d, J7Hz, $CH_3$), 1.24 (3H, d, J7Hz, $CH_3$), 1.86 (3H, d, $j_{12-CH_3,13}$ 1Hz, 12-$CH_3$), 2.15 (3H, s, 3—$OCOCH_3$), 2.52 (6H, s, 3'—$N(CH_3)_2$), 4.18 (1H, d, $J_{1'ax,2'ax}$ 7Hz, $H_{1'ax}$), 5.95 (1H, dq, $J_{12-CH_3,13}$ 1Hz, $J_{13,14}$ 10Hz, $H_{13}$), 6.31 (1H, d, $J_{10,11}$ 16Hz, $H_{10}$), 7.43 (1H, d, $J_{10,11}$ 16Hz, $H_{11}$) and 9.64 (1H, s, $H_{20}$).

(e) 3,2'-Di-O-acetyl-4''-O-iso-valeryltylosin (2 g, 0.0019 mole) and 1-N-ethyl-3-N-(3-dimethylaminopropyl)carbodiimide hydrochloride (4.24 g, 0.0222 mole) were dissolved in dry dimethylsulfoxide (53 ml). The solution was stirred under argon at 24° C. and pyridine (0.6 ml, 0.0075 mole) and trifluoroacetic acid (0.28 ml, 0.0037 mole) in dry dimethylsulfoxide (2 ml) were added. The mixture was stirred at 25° C. for 36 hours and then evaporated to dryness under high vacuum. The residue was taken up in dichloromethane and washed with water, the pH being adjusted to 9.3. The dichloromethane layer was dried ($MgSO_4$), filtered and evaporated to dryness. The residue was chromatographed on a silica gel column (120×2 cm) using 8% acetone in dichloromethane as the eluant to afford 3,2'-di-O-acetyl-23-O-demycinosyl-4''-O-iso-valeryltylosn (1.21 g, 70%) as a colorless amorphous solid, (Found: C, 56.38; H, 6.99; N, 1.22. $C_{47}H_{75}NO_{16}$0.8$CHCl_3$ requires: C, 56.24; H, 7.52; N, 1.39%), m/z 910 (MH+), $[\alpha]_D^{26}$ −40.6° ($CHCl_3$), λmax ($CF_3CH_2OH$) 284 nm ( 16,890), λmax ($CDCl_3$) 3490, 1737, 1680, 1595, 1238, 1167, 1059, 1029 cm.$^{-1}$, $\delta_H$ ($CDCl_3$) 0.93 (3H, t, $J_{16,17-CH_3}$ 7Hz, 17—$CH_3$), 0.98 (6H, d, J7Hz, ''—$OCOCH_2CH(CH_3)_2$), 1.13 (3H, s, 3''—$CH_3$), 1.14 (3H, d, J7Hz, $CH_3$), 1.22 (3H, d, J7Hz, $CH_3$), 1.86 (3H, d, $J_{12-CH_3,13}$ 1Hz, 12—$CH_3$), 2.07 (3H, s, 2'—$OCOCH_3$), 2.14 (3H, s, 3—$OCOCH_3$), 2.42 (6H, s, 3'—$N(CH_3)_2$), 4.27 (1H, d, $J_{1'ax,2'ax}$ 8Hz, $H_{1'ax}$), 5.92 (1H, dq, $J_{12-CH_3,13}$ 1Hz, $J_{13,14}$ 10Hz, $H_{13}$), 6.34 (1H, d, $J_{10,11}$ 15.5Hz, $H_{10}$), 7.43 (1H, d, $J_{10,11}$ 15.5Hz, $H_{11}$) and 9.63 (H, s, $H_{20}$).

(iv)

3-O-Acetyl-23-O-demycinosyl-4''-O-iso-valeryltylosin 3,2'-Di-O-acetyl-23-O-demycinosyl-4''-O-iso-valeryltylosin (944 mg) was dissolved in methanol (120 ml) and the solution was allowed to remain at 40° C. for 40 h. Evaporation, followed by chromatography on a silica gel column (60×2 cm) using 15% acetone in hexane as the eluant, gave 3-O-acetyl-23-O-demycinosyl-4''-O-iso-valeryltylosin (894 mg, 91%) M/Z 868 (MH+) which was identical with that described earlier in Example 2 (iii)(d).

(v)

3,2'-Di-O-acetyl-23-O-demycinosyl-20-deoxo-20-[(4,4-dioxothiomorpholinyl)imino]-4''-O-iso-valeryltylosin and 3-O-acetyl-23-O-demycinosyl-20-deoxo-20-[(4,4-dioxothiomorpholinyl)imino]-4''-O-iso-valeryltylosin (a) 3,2'-Di-O-acetyl-4''-O-iso-valeryltylosin (400 mg) and 1-N-amino-4,4-dioxothiomorpholine (111 mg) were dissolved in dry tetrahydrofuran (35 ml) and the mixture was stirred under argon at 25° C. for 19 h. The solution was evaporated to dryness and the residue was chromatographed on a silica gel column (15×2 cm) using 25% acetone in hexane as the eluant to give 3,2'-di-O-acetyl-20-deoxo-20-[(4,4-dioxothiomorpholinyl)imino]-4''-O-iso-valeryltylosin (396 mg, 88%) as a colourless amorphous solid.

1-N-Ethyl-3-N-(3-dimethylaminopropyl)-carbodiimide hydrochloride (750 mg, 0.0040 mole) was dissolved in dry dimethylsulfoxide (10 ml) and the hydrazone (396 mg, 0.0004 mole) was added. The solution was stirred under argon at 25° C. and a mixture of pyridine (0.105 ml, 0.0013 mole) and trifluoroacetic acid (0.050 ml, 0.0007 mole) in dry dimethylsulfoxide (0.8 ml) was added. The mixture was stirred at 25° C. for 19 h. The solution was evaporated to dryness under high vacuum and the residue was taken up in dichloromethane and washed with water, the pH being adjusted to 9.0. The dichloromethane layer was dried ($MgSO_4$), filtered and evaporated to dryness. The residue was taken up in methanol (50 ml) containing triethylamine (2 ml) and the mixture was stirred at 25° C. for 25 h. The solution was evaporated to dryness and the residue was chromatographed on a silica gel column (30×2 cm) using 22% acetone in hexane as the eluant to give 3,2'-di-O-acetyl-23-O-demycinosyl-20-deoxo-20-[(4,4-dioxothiomorpholinyl)-imino]-4''-O-iso-valeryltylosin (97 mg, 29%) as a colorless amorphous solid, (Found: C, 58.70; H, 7.12; N, 4.70; S, 3.14. $C_{51}H_{83}N_3O_{17}S$ requires: C, 58.77; H, 8.03; N, 4.03; S, 3.08%), m/z 1042 (MH+), $[\alpha]_D^{26}$ −93.7° ($CHCl_3$), λmax ($CH_3OH$) 240 nm ( 7,834), 282 nm ( 20,986), λmax ($CDCl_3$) 3600, 3490, 1736, 1675, 1592, 1240, 1185, 1176, 1122, 1050, 1026 cm.$^{-1}$, $\delta_H$ ($CDCl_3$) 0.91 (3H, t, $J_{16,17-CH_3}$ 7Hz, 17—$CH_3$), 0.97 (6H, d, J7Hz, 4''—$OCOCH_2CH(CH_3)_2$), 1.10 (3H, s, 3''—$CH_3$), 1.12 (3H, d, J7Hz,$CH_3$) 1.22 (3H, d, J7Hz, $CH_3$), 1.27 (3H, d, J7Hz, $CH_3$), 1.83 (3H, d, $J_{12-CH_3,13}$ 1Hz, 12—$CH_3$), 2.04 (3H, s, 2'—$OCOCH_3$), 2.10 (3H, s, 3—$OCOCH_3$), 2.42 (6H, s, 3'—$N(CH_3)_2$), 4.26 (1H, d, $J_{1'ax,2'ax}$ 8Hz, $H_{1'ax}$), 5.92 (1H, dq, $J_{12-CH_3,13}$ 1Hz, $J_{13,14}$ 10Hz, $H_{13}$), 6.29 (1H, d, $J_{10,11}$ 15.5Hz, $H_{10}$), 7.04 (1H, dd, $J_{19,20}=J_{19'20}=$4Hz, $H_{20}$) and 7.42 (1H, d, $J_{10,11}$ 15.5Hz, $H_{11}$) and 3-O-acetyl-23-O-demycinosyl-20-deoxo-20-[(4,4-dioxothiomorpholinyl)-imino]-4''-O-iso-valeryltylosin (47 mg, 15%) as a colorless amorphous solid, (Found: C, 57.62; H, 7.65; N, 4.11; S, 3.49. $C_{49}H_{81}N_3O_{16}S$ . 0.2 $CHCl_3$ requires: C, 57.47; H, 7.97; N, 4.10; S, 3.13%) m/z 1000 (MH+), $[\alpha]_D^{26}$ −85.8° ($CHCl_3$), λmax ($CH_3OH$) 239 nm ( 8,200), 282nm (20,713), max ($CDCl_3$) 3600, 3482, 1733, 1675, 1591, 1308, 1250, 1185, 1175, 1122, 1050, 1027 cm.$^{-1}$, $\delta_H$ ($CDCl_3$) 0.92 (3H, t, $J_{16,17-CH_3}$ 7Hz, 17—$CH_3$), 0.98 (6H, d, J7Hz, 4''—$OCOCH_2CH(CH_3)_2$), 1.06 (3H, d, J7Hz,$CH_3$) 1.11 (3H, s, 3″—CH$_3$), 1.14 (3H, d, J7Hz, CH$_3$), 1.86 (3H, d, J$_{12-CH3,13}$ 1Hz, 12—CH$_3$), 2.05 (3H, s, 3—OCOCH$_3$), 2.55 (6H, s, 3′—N(CH$_3$)$_2$), 4.19 (1H, d, J$_{1'ax,2'ax}$ 8Hz, H$_{1'ax}$), 5.96 (1H, dq, J$_{12-CH3,13}$ 1Hz, J$_{13,14}$ 10Hz, H$_{13}$), 6.31 (d, J$_{10,11}$ 15.5Hz, H$_{10}$), 7.04 (1H, dd, J$_{19,20}$=J$_{19',20}$=4Hz H$_{20}$) and 7.44 (1H, d, J$_{10,11}$ 15.5Hz, H$_{11}$).

(b) 3,2′-Di-O-acetyl-23-O-demycinosyl-4″-O-iso-valeryltylosin (600 mg) and 1-N-amino-4,4-dioxothiomorpholine (198 mg) were dissolved in dry tetrahydrofuran (20 ml) and the mixture was stirred under argon at 25° C. for 20 h. The solution was evaporated to dryness and the residue was chromatographed on a silica gel column (60×2 cm) using 15% acetone in hexane as the eluant to give 3,2′-di-O-acetyl-23-O-demycinosyl-20-deoxo-20-[(4,4-dioxothiomorpholinyl)imino-4″-O-iso-valeryltylosin (496 mg, 72%) which was identical with that prepared above.

(c) 3-O-Acetyl-23-O-demycinosyl-4″-O-iso-valeryltylosin (450 mg) and 1-N-amino-4,4-dioxothiomorpholine (156 mg) were dissolved in dry tetrahydrofuran (80 ml) and the mixture was stirred under argon at 25° C. for 121 h. The solution was evaporated to dryness and the residue was chromatographed on a silica gel column (120×2 cm) using 20% acetone in hexane as the eluant to give 3-O-acetyl-23-O-demycinosyl-20-deoxo-20-[(4,4-dioxothiomorpholinyl)imino]-4″-O-iso-valeryltylosin (441 mg, 85%) that was identical with that prepared in 2 (vi) above.

(vi)
3,23,2′-Tri-O-acetyl-23-O-demycinosyl-4″-O-iso-valeryltylosin.

3-O-Acetyl-23-O-demycinosyl-4″-O-iso-valeryltylosin (1.2 g, 0.0014 mole) 4-dimethylaminopyridine (33 mg, 0.003 mole), pyridine (1.07 ml, 0.0133 mole) and acetic anhydride (0.62 ml, 0.0066 mole) were dissolved in dry dichloromethane (200 ml) and the solution was allowed to stir at 25° C. under dry argon for 43 h. The mixture was poured into water at pH 10 and extracted with dichloromethane. The organic layer was dried (MgSO$_4$), filtered and evaporated to dryness. The residue was azeotroped with toluene and chromatographed on silica gel column (30×2 cm) using 15%) acetone in hexane as the eluant to give 3,23,2′-tri-O-acetyl-23-O-demycinosyl-4″-O-iso-valeryltylosin as a colorless amorphous solid, (Found: C, 61.66; H, 8.25; N, 0.98 . C$_{49}$H$_{77}$NO$_{17}$ requires: C, 61.81; H, 8.15; N, 1.47%), m/z 952 (MH$^+$), [α]$_D^{26}$ −47.5° (CHCl$_3$), λmax (CF$_3$CH$_2$OH) 282 nm ( 21,504), λmax (CDCl$_3$) 3470, 1730, 1595, 1240, 1166, 1120, 1058, 1028 cm.$^{-1}$, δ$_H$ (CDCl$_3$) 0.93 (3H, t, J$_{16,17-CH3}$ 7Hz, 17—CH$_3$), 0.98 (6H, d, J7Hz, 4″—OCOCH$_2$CH(CH$_3$)$_2$), 1.11 (3H, s, 3‴—CH$_3$), 1.13 (3H, d, J7Hz, CH$_3$), 1.22 (3H, d, J7Hz, CH$_3$), 1.83 (3H, d, J$_{12-CH3,13}$ 1Hz, 12—CH$_3$), 2.06 (3H, s, 3—OCOCH$_3$), 2.08 (3H, s, 2′—OCOCH$_3$), 2.14 (3H, s, 4‴—OCOCH$_3$), 2.42 (6H, s, 3′—N(CH$_3$)$_2$), 4.64 (1H, d, J$_{1'ax,2'ax}$ 8Hz, H$_{1'ax}$), 5.88 (1H, dq, J$_{12-CH3,13}$ [1Hz, J$_{13,14}$ 10Hz, H$_{13}$), 6.34 (1H, d, J$_{10,11}$ 15.5Hz, H$_{10}$), 7.42 (1H, d, J$_{10,11}$ 15.5Hz, H$_{11}$) and 9.63 (1H, s, H$_{20}$). (vii) 3,23,2′-Tri-O-acetyl-23-O-demycinosyl-20-deoxo-20-[(4,4-dioxothiomorpholinyl)imino]-4″-O-iso-valeryltylosin 3,23,2′-Tri-O-acetyl-23-O-demycinosyl-4″-O-iso-valeryltylosin (517 mg) and 1-N-amino-4,4-dioxothiomorpholine (163 mg) were dissolved in dry tetrahydrofuran (20 ml) and the mixture was stirred at 25° C. under dry argon for 19 hours. The solution was evaporated to dryness and the residue was chromatographed on a silica gel column (30×2 cm) using 15% acetone in hexane as the eluant to give 3,23,2′-tri-O-acetyl-23-O demycinosyl-20-deoxo-20-[(4,4-dioxothiomorpholinyl)imino]-4″-O-iso-valeryltylosin (538 mg, 91%) as a colorless amorphous solid, (Found: C, 58.56; H, 7.92; N, 3.73, C$_{53}$H$_{85}$N$_3$O$_{18}$S requires: C, 58.71; H, 7.90; N, 3.88%), m/z 1084 (MH$^+$) [α]$_D^{26}$ −110.0° (CHCl$_3$), λmax (CF$_3$CH$_2$OH) 237 nm ( 7,977), 281 nm ( 22,227), λmax (CDCl$_3$) 3490, 1740, 1593, 1312, 1242, 1187, 1177, 1127, 1058, 1030, cm$^{-1}$, δ$_H$ (CDCl$_3$) 0.94 (3H, t, J$_{16,17-CH3}$ 7Hz, 17—CH$_3$), 0.97 (6H, d, J7Hz, 4″—OCOCH$_2$CH(CH$_3$)$_2$), 1.12 (3H, s, 3‴—CH$_3$), 1.13 (3H, d, J7Hz, CH$_3$), 1.22 (3H, d, J7Hz, CH$_3$), 1.82 (3H, d, J$_{12-CH3,13}$ 1Hz, 12—CH$_3$), 2.04 (3H, s, 3—OCOCH$_3$), 2.06 (3H, s, 2′—OCOCH$_3$), 2.08 (3H, s, 23—OCOCH$_3$), 2.41 (6H, s, 3′—N(CH$_3$)$_2$), 5.88 (1H, dq, J$_{12-CH3, 13}$ 1Hz, J$_{13,14}$ 10.5Hz, H$_{13}$), 6.28 (1H, d, J$_{10,11}$ 16 Hz, H$_{10}$), 7.00 (1H, dd, J$_{19,20}$=J$_{19',20}$=3.5Hz, H$_{20}$) and 7.38 (1H, d, J$_{10,11}$ 16Hz, H$_{11}$).

(viii)
3,23-Di-O-acetyl-23-O-demycinosyl-20-deoxo-20-[(4,4-dioxothiomorpholinyl)imino]-4″-O-iso-valeryltylosin 3,2′-Di-O-acetyl-23-O-demycinosyl-4″-O-iso-valeryltylosin (550 mg, 0.0006 mole) 4-dimethylaminopyridine (14.8 mg, 0.0002 mole), pyridine (0.5 ml, 0.0063 mole) and acetic anhydride (0.28 ml, 0.0030 mole) were dissolved in dry dichloromethane (80 ml.) and the mixture was stirred under argon at 25° C. for 20 hours. The mixture was diluted with dichloromethane and water and the pH was adjusted to 10. The dichloromethane extract was dried (MgSO$_4$), filtered and evaporated to dryness. The residue was chromatographed on a silica gel column (60×2 cm.) using 15% acetone in hexane as the eluant to give 3,23,2′-tri-O-acetyl-23-O-demycinosyl-4″-O-iso-valeryltylosin (548 mg., 95%) as a colourless amorphous solid, m/z 952 (MH$^+$).

The latter (548 mg.) was dissolved in methanol (70 ml.) and the mixture was heated under reflux at 40° C. for 9 hours. The solution was evaporated to dryness and the residue was chromatographed on a silica gel column (60×2 cm.) using 18% acetone in hexane as the eluant to give 3,23-di-O-acetyl-23-O-demycinosyl-4″-O-iso-valeryltylosin (470 mg., 82%) as a colourless amorphous solid.

The aldehyde (470 mg.) and 1-N-amino-4,4-dioxothiomorpholine (156 mg.) were dissolved in dry tetrahydrofuran (60 ml.) and the mixture was stirred under argon at 25° C. for 19 hours. The solution was evaporated to dryness and the residue was chromatographed on a silica gel column (30×2 cm.) using 20% acetone in hexane as the eluant to give 3,23-di-O-acetyl-23-O-demycinosyl-20-deoxo-20-[(4,4-dioxothiomorpholinyl)imino]-4″-O-iso-valeryltylosin (422 mg., 78%) as a colourless amorphous solid, (Found: C, 57.35; H, 7.87; N, 3.88). C$_{51}$H$_{83}$N$_3$O$_{17}$S requires: C, 57.45; H, 7.85; N, 3.94%), m/z 1042 (MH$^+$), [α]$_D^{26}$ −101.9° (CHCl$_3$), λmax (CH$_3$OH) 238 nm ( 10,303), 280 nm ( 21,735), λmax (CDCl$_3$) 3435, 1728, 1672, 1588, 1305, 1242, 1180, 1165, 1120, 1050, 1023 cm.$^{-1}$, δ$_H$ (CDCl$_3$) 0.94 (3H, t, J$_{16-CH3,17}$ 7Hz, 17—CH$_3$), 0.98 (6H, d, J 7Hz, 4″—OCOCH$_2$CH(CH$_3$)$_2$), 1.06 (3H, d, J 7Hz, CH$_3$), 1.13 (3H, s, 3‴—CH$_3$), 1.14 (3H, d, J 7Hz, CH$_3$), 1.22 (3H, d, J 7Hz, CH$_3$), 1.83 (3H, d, J$_{12-CH3}$, 1Hz, 12—CH$_3$), 2.03 (3H, s, 23—OCOCH$_3$), 2.05 (3H, s, 3—OCOCH$_3$), 2.52 (6H, s, 3′—N(CH$_3$)$_2$), 5.91 (1H, dq, J$_{12-CH3,13}$ 1Hz, J$_{13,14}$ 10 Hz, H$_{13}$), 6.31 (1H, d, J$_{10,11}$ 15.5 Hz, H$_{10}$), 7.02

(1H, dd, $J_{19,20}=J_{19',20}=4$ Hz, $H_{20}$) and 7.43 (1H, $J_{10,11}$ 15.5 Hz, $H_{11}$).

(ix)
3,2'-Di-O-acetyl-23-O-demycinosyl-23-O-phenylacetyl-4"-O-iso-valeryltylosin 3,2'-Di-O-acetyl-23-O-demycinosyl-4"-O-iso-valeryltylosin (599 mg, 0.0007 mole), pyridine (0.293 ml, 0.0037 mole) and phenylacetyl chloride (0.1917 ml, 0.0015 mole) were dissolved in dry dichloromethane (15 ml) and the mixture was allowed to stand at $-7°$ C. under dry argon for 20 hours. Additional phenylacetyl chloride (0.1150 ml, 0.0009 mole) was added and the reaction was continued for a total of 42 hours. The mixture was poured into water at pH 10 and extracted with dichloromethane. The organic layer was dried (MgSO$_4$), filtered and evaporated to dryness. The residue was chromatographed on a silica gel column (60×2 cm) using 15% acetone in hexane as the eluant to give 3,2'-di-O-acetyl-23-O-demycinosyl-23-O-phenylacetyl-4"-O-iso-valeryltylosin (604 mg, 89%) as a colorless amorphous solid, m/z 1029 (MH$^+$), $\delta_H$ (CDCl$_3$) 0.89 (3H, t, $J_{16,17-CH_3}$ 7Hz, 17—CH$_3$), 1.00 (6H, d, J7Hz, 4"—OCOCH$_2$CH(CH$_3$)$_2$), 1.08 (6H, d, J7Hz, CH$_3$), 1.24 (3H, d, J7Hz, CH$_3$), 1.74 (3H, d, $J_{12-CH_3,13}$ 1Hz, 12—CH$_3$), 2.06 (3H, s, 3—OCOCH$_3$), 2.14 (3H, s, 2'—OCOCH$_3$), 2.43 (6H, s, 3'—N(CH$_3$)$_2$), 3.61 (2H, s, 23—OCOCH$_2$C$_6$H$_5$), 5.80 (1H, dq, $J_{12-CH_3,13}$ 1Hz, $J_{13,14}$ 10Hz, H$_{13}$), 6.28 (1H, d, $J_{10,11}$ 15.5Hz, H$_{10}$), 7.29 (5H, bs, 23—OCOCH$_2$C$_6$H$_5$), 7.34 (1h, d, $J_{10,11}$ 15.5Hz,H$_{11}$) and 9.63 (1H, s, H$_{20}$).

(x)
3-O-Acetyl-23-O-demycinosyl-23-O-phenylacetyl-4"-O-iso-valeryltylosin.

3,2'-Di-O-acetyl-23-O-demycinosyl-23-O-phenylacetyl-4"-O-iso-valeryltylosin (581 mg) was dissolved in methanol (70 ml) and the solution was heated at 50° C. under reflux for 7 hours. The solution was evaporated to dryness and the residue was chromatographed on a silica gel column (15×2.5 cm.) using 17% acetone in hexane as the eluant to give 3-O-acetyl-23-O-demycinosyl-23-O-phenyacetyl-4"-O-iso-valeryltylosin (500 mg, 90%) as a colorless amorphous solid.

(xi)
3-O-Acetyl-23-O-demycinosyl-20-deoxo-20-[(4,4-dioxothiomorpholinyl)imino]-23-O-phenylacetyl-4"-O-iso-valeryltylosin.

3-O-Acetyl-23-O-demycinosyl-23-O-phenylacetyl-4"-O-iso-valeryltylosin (418 mg) and 1-N-amino-4,4-dioxothiomorpholine (75 mg) were dissolved in dry tetrahydrofuran (50 ml) and the solution was stirred at 25° C. for 20 hours. The solution was evaporated to dryness and the residue was chromatographed on a silica gel column (15×2 cm) using 16% acetone in hexane as the eluant to give 3-O-acetyl-23-O-demycinosyl-20-deoxo-20-[(4,4-dioxothiomorpholinyl(imino]-23-O-phenylacetyl-4"-O-iso-valeryltylosin (416 mg, 89%) as a colorless amorphous solid, (Found: C, 61.01; H, 7.94; N, 3.06, . C$_{57}$H$_{87}$N$_3$O$_{17}$S requires; C, 61.21; H, 7.84; N, 3.76%), m/z 1118 (MH$^+$) $[\alpha]_D^{26}$ $-76.8°$ (CHCl$_3$), $\lambda$max (CH$_3$OH) 241 nm ( 7,283), 281 nm ( 20,651), $\lambda$max (CDCl$_3$) 3460, 1730, 1677, 1592, 1305, 1247, 1183, 1163, 1122, 1052, 1017, cm.$^{-1}$, $\delta_H$ (CDCl$_3$) 0.88 (3H, t, $J_{16,17-CH_3}$ 7Hz, 17—CH$_3$), 0.98 (6H, d, J7Hz, 4"—O-COCH$_2$CH(CH$_3$)$_2$), 1.06 (3H, d, J7Hz CH$_3$), 1.11 (3H, s, 3"—CH$_3$), 1.14 (3H, d, J7Hz, CH$_3$), 1.23 (3H, d, J7Hz, CH$_3$), 1.30 (3H, d, J6Hz, CH$_3$), 2.02 (3H, s, 3—OCOCH$_3$), 2.52 (6H, s, 3'—N(CH$_3$)$_2$), 3.60 (2H, s, 20—O-COCH$_2$C$_6$H$_5$), 5.83 (1H, dq, $J_{12-CH_3,13}$ 1Hz, $J_{13,14}$ 10.5Hz, H$_{13}$), 6.26 (1H, d, $J_{10,11}$ 16 Hz, H$_{10}$), 7.00 (1H, dd, $J_{19,20}=J_{19',20}=3$Hz, H$_{20}$), 7.28 (5H, bs, 20—O-COCH$_2$C$_6$H$_5$) and 7.36 (1H, d, $J_{10,11}$ 16Hz, H$_{11}$).

"Drug" used in the following examples refers to the di-and tri-O-acetyl-23-O-Demycinosyl-4"-O-Iso-valeryl tylosins prepared in the Examples 2 (iii)(e), 2 (iv) and 2 (vi).

EXAMPLE 3

| Capsule | |
| --- | --- |
| Drug | 250.00 mg |
| Lactose | 248.75 mg |
| Magnesium Stearate | 1.25 mg |
| | 500.00 mg |

Procedure

1. Blend the drug and the lactose.
2. Add the magnesum stearate and mix.
3. Fill capsule.

EXAMPLE 4

| Oral suspension (to give a dose of 125 mg/5 ml) | |
| --- | --- |
| Drug | 25.00 gms |
| Magnesium Aluminum Silicate | 9.50 gms |
| Sodium carboxymethyl cellulose USP (CMC) | 2.50 gms |
| Flavor | q.s. |
| Color | q.s. |
| Methyl paraben U.S.P. | 0.90 gms |
| Propyl paraben U.S.P. | 0.20 gms |
| Polysorbate 80, U.S.P.* | 1.00 gms |
| Sorbitol Solution, U.S.P. | 500.00 gms |
| Water, q.s. | 1000.00 ml. |

*Polysorbate 80 is a mixture of oleate esters of sorbitoland sorbitol anhydrides, consisting predominantly of the monoester, condensed with approximately 20 mls of ethylene oxide.

Procedure

1. Heat 200 ml. of water to boiling, and dissolve it in one half of the parabens. Cool to about 70° C., then mix in the polysorbate 80. Sprinkle in the silicate, stirring until a uniform smooth suspension results.
2. Heat an additional 200 ml. of water to boiling, and dissolve in it the remainder of the parabens. Disperse the CMC in this until a smooth gel results. Mix in the sorbitol solution. Then dissolve the sodium citrate therein.
3. Add the product of Step 2 to that of Step 1 slowly, with constant stirring. Cool the mixture to 25° C. Add the drug, tartrate flavor, and color, mixing thoroughly. Add sufficient quantity of water to make the total volume 1000 ml.

EXAMPLE 5

| Topical Ointment | |
| --- | --- |
| Drug | 10 gms |
| Petrolatum | 990 gms |
| | 1000 gms |

Procedure

1. Melt the petrolatum.
2. Slurry the drug with about 10% of the petrolatum and pass through a colloid mill.
3. Mix the milled slurry with the remainder of the molten petrolatum. Allow to cool.

EXAMPLE 6

| Topical Cream | |
|---|---|
| Drug | 10 gms |
| Stearic acid | 200 gms |
| Sorbitan monostearate | 104 gms |
| Sorbitan monoleate | 20 gms |
| Polyoxyethylene sorbitan monolaurate | 56 gms |
| Water, q.s. | 100 mls |

PROCEDURE

1. Heat the stearic acid, sorbitan monostearate, sorbitan monoleate and polyoxyethylene sorbitan monolaureate to 65° C.
2. Heat about 90% of the water to 70° C.
3. Add the water to Step 1 and mix to form a cream base.
4. Slurry the drug with about 10% of the water and pass through a colloid mill.
5. Add the milled slurry to the molten base and mix. Allow to cool.

We claim:

1. A process for selectively deacylating the 2' and 4''''-positions in 3,2',4'',4''''-tetra-O-acyltylosin or 2',4'',4''''-tri-O-acyltylosin which comprises treating 3,2',4'',4''''-tetra-O-acyltylosin or 2',4'',4''''-triacyltylosin with a deblocking reagent consisting essentially of an organic trisubstituted nitrogen base and a lower alkanol to produce 3,4''-di-O-acyltylosin or 4''-O-acyltylosin substantially free of side products.

2. A process of claim 1 wherein the starting material is 3,2',4'',4''''-tetra-O-acyltylosin and the product is 3,4''-di-O-acyltylosin.

3. A process of claim 1 wherein the starting material is 2',4'',4''''-tri-O-acyltylosin and the product is 4''-O-acyltylosin.

4. A process of claim 1 wherein the acyl group at the 4''-position is an iso-valeryl group.

5. A process for preparing 3,23,2',4''-tetra-O-acyl-23-O-demycinosyltylosin from tylosin which comprises:

(a) treating tylosin with an acylating agent in an aprotic solvent in the absence of externally added base to produce 2'-O-acyltylosin;

(b) treating the reaction mixture of step (a) with an acylating agent, and a 4-disubstitutedaminopyrdine in the presence of externally added base to produce 2',4''''-di-O-acyltylosin;

(c) treating the product of step (b) with about a stoichiometric amount of an acylating agent in the presence of more than about 0.1 to about 1 mole of a 4-disubstituted/aminopyridine per mole of acylating agent and an externally added base to produce 2',4'',4''''-tri-O-acyltylosin substantially free of 3-O-acyltylosin and 3''-O-acyltylosin products;

(d) treating the product of step (c) with at least about a stoichiometric amount of an acylating agent and about 0.5 to about 1.5 moles of a 4-disubstitutedaminopyridine per mole of acylating agent in the presence of externally added base to produce 3,2',4'',4''''-tetra-O-acyltylosin substantially free of 3''-O-acyltylosin products;

(e) selectively deacylating the 2' and 4''''-position of the product of step (d) by treating the product of step (d) with a deblocking reagent consisting essentially of an organic tri-substituted nitrogen base and a lower alkanol to produce 3,4''-di-O-acyltylosin substantially free of side products;

(f) treating the product of step (e) with an acylating agent in an aprotic solvent in the absence of externally added base to produce 3,2',4''-O-triacyltylosin;

(g) selectively removing the mycinosyl group at the 23 position to produce 3,2',4''-tri-O-acyl-23-O-demycinosyltylosin; and (h) treating the product of step (g) with an acylating agent in the presence of a 4-disubstitutedaminopyridine and externally added base to produce 3,23,2',4''-tetra-O-acyl-23-O-demycinosyltylosin.

6. A process of claim 5 wherein the acyl group in the 4''-position is an iso-valeryl group.

7. A process of claim 5 wherein the acylating agent in steps (a), (b), (d), (f) and (h) is acetic anhydride.

8. A process for preparing 3,2',4''-tri-O-acyl-23-O-demycinosyltylosin from tylosin which comprises:

(a) treating tylosin with an acylating agent in an aprotic solvent in the absence of externally added base to produce 2'-O-acyltylosin;

(b) treating the reaction mixture of step (a) with an acylating agent, and a 4-disubstituted amino-pyridine in the presence of externally added base to produce 2',4''''-di-O-acyltylosin;

(c) treating the product of step (b) with about a stoichiometric amount of an acylating agent in the presence of more than about 0.1 to about 1 mole of a 4-disubstitutedaminopyridine per mole of acylating agent and an externally added base to produce 2',4'',4''''-tri-O-acyltylosin substantially free of 3-O-acyltylosin or 3''-O-acyltylosin products or 3-O-acyltylosin and 3''-O-acyltylosin products;

(d) treating the product of step (c) with at least about a stoichiometric amount of an acylating agent and about 0.5 to about 1.5 moles of a 4-disubstituted aminopyridine per mole of acylating agent in the presence of externally added base to produce 3,2',4'',4''''-tetra-O-acyltylosin products substantially free of 3''-O-acyltylosin products;

(e) selectively deacylating the 2' and 4''''-positions of the product of step (d) by treating the product of step (d) with a deblocking reagent consisting essentially of an organic tri-substituted nitrogen base and a lower alkanol to produce 3,4''-di-O-acyltlosin substantaily free of side products;

(f) treating the product of step (e) with an acylating agent in an aprotic solvent in the absence of externally added base to produce 3,2',4''-O-triacyltylosin; and (g) selectively removing the mycinoasyl group at the 23 position to produce 3,2',4''-tri-O-acyl-23-O-demycinosyltylosin.

9. A process of claim 8 wherein the acyl group in the 4''-position is an iso-valeryl group.

10. A process of claim 8 wherein the acylating agent in steps (a), (b), (d), and (f) is acetic anhydride.

* * * * *